(12) United States Patent
Hamilton et al.

(10) Patent No.: US 6,677,376 B1
(45) Date of Patent: Jan. 13, 2004

(54) NON-PEPTIDIC CYCLOPHILIN BINDING COMPOUNDS AND THEIR USE

(75) Inventors: Gregory S. Hamilton, Catonsville, MD (US); Joseph P. Steiner, Mt. Airy, MD (US); Mark J. Vaal, Baltimore, MD (US); Chi Choi, Towson, MD (US); Ling Wei, Lutherville, MD (US)

(73) Assignee: Guilford Pharmaceuticals, Inc., Baltimore, MD (US)

( * ) Notice: Subject to any disclaimer, the term of this patent is extended or adjusted under 35 U.S.C. 154(b) by 0 days.

(21) Appl. No.: 09/656,898

(22) Filed: Sep. 7, 2000

Related U.S. Application Data

(63) Continuation-in-part of application No. 09/392,290, filed on Sep. 8, 1999, now abandoned.

(51) Int. Cl.[7] .............................................. A61K 31/18

(52) U.S. Cl. ............................ 514/603; 514/9; 514/11; 514/19; 514/604; 514/605; 514/616; 514/619; 514/621; 514/622; 514/626; 514/629; 514/688; 514/689; 514/718; 514/731; 530/317; 564/86

(58) Field of Search ............................ 564/86; 514/603, 514/9, 11, 19, 604, 605, 616, 619, 621, 622, 626, 629, 688, 689, 718, 731; 530/317

(56) References Cited

U.S. PATENT DOCUMENTS

| | | |
|---|---|---|
| 2,328,490 A | 8/1943 | Pöhls |
| 2,333,552 A | 11/1943 | Pöhls |
| 2,395,484 A | 2/1946 | Jennings |
| 2,635,535 A | 4/1953 | Jennings |
| 2,714,613 A | 8/1955 | Huebner |
| 3,673,241 A | 6/1972 | Marxer |
| 3,821,200 A | 6/1974 | Stingl |
| 3,829,463 A | 8/1974 | Kornis |
| 3,829,464 A | 8/1974 | Kornis |
| 3,867,426 A | 2/1975 | Olin |
| 3,872,157 A | 3/1975 | Brokke |
| 3,880,642 A | 4/1975 | Baker |
| 3,937,729 A | 2/1976 | Teach |
| 3,941,581 A | 3/1976 | Teach |
| 3,962,306 A | 6/1976 | Kuhle |
| 3,981,914 A | 9/1976 | Mutsch |
| 4,028,093 A | 6/1977 | Teach |
| 4,031,127 A | 6/1977 | Leone |
| 4,041,070 A | 8/1977 | Asato |
| 4,044,147 A | 8/1977 | Nelson |
| 4,072,711 A | 2/1978 | Asato |
| 4,111,682 A | 9/1978 | Gutman |
| 4,225,708 A | 9/1980 | Kanbe |
| 4,238,503 A | 12/1980 | Teach |
| 4,245,037 A | 1/1981 | Tsujino |
| 4,255,511 A | 3/1981 | Hirano |
| 4,266,013 A | 5/1981 | Adachi |
| 4,282,369 A | 8/1981 | Schirmer |
| 4,328,165 A | 5/1982 | Schirmer |
| 4,328,367 A | 5/1982 | Nagase |
| 4,373,017 A | 2/1983 | Masukawa |
| 4,384,999 A | 5/1983 | Bollinger |
| 4,387,106 A | 6/1983 | De Vries |
| 4,405,644 A | 9/1983 | Kabbe |
| 4,410,697 A | 10/1983 | Török |
| 4,426,222 A | 1/1984 | Brorschewski |
| 4,435,567 A | 3/1984 | Lugosi |
| 4,473,579 A | 9/1984 | De Vries |
| 4,536,341 A | 8/1985 | Rigterink |
| 4,544,654 A | 10/1985 | Davey |
| 4,608,082 A | 8/1986 | Craig |
| 4,623,662 A | 11/1986 | De Vries |
| 4,629,739 A | 12/1986 | Davey |
| 4,681,871 A | 7/1987 | Teschemacher |
| 4,703,033 A | 10/1987 | Seebach |
| 4,711,905 A | 12/1987 | Sirrenberg |
| 4,764,503 A | 8/1988 | Wenger |
| 4,820,871 A | 4/1989 | Kissener |
| 4,855,478 A | 8/1989 | Woolard |
| 4,868,210 A | 9/1989 | Trivedi |
| 4,885,276 A | 12/1989 | Witzel |
| 4,914,188 A | 4/1990 | Dumont |

(List continued on next page.)

FOREIGN PATENT DOCUMENTS

| | | |
|---|---|---|
| EP | 0 053 029 | 6/1982 |
| EP | 0 633 145 | 1/1995 |
| WO | WO 88/06451 | 9/1988 |
| WO | WO 92/04370 | 3/1992 |
| WO | WO 92/19254 | 11/1992 |
| WO | WO 96/40633 | 12/1996 |
| WO | WO 97/18828 | 5/1997 |
| WO | WO 97/36869 | 10/1997 |
| WO | WO 98/25950 | 6/1998 |
| WO | WO 98/37882 | 9/1998 |
| WO | WO 98/45259 | 10/1998 |
| WO | WO 99/00357 | 1/1999 |
| WO | WO 99/15164 | 4/1999 |
| WO | WO 99/59959 | 11/1999 |
| WO | WO 01/17953 | 3/2001 |

OTHER PUBLICATIONS

Chandrakumar et a., Chamical Abstracts, vol. 130:25348, 1998.*
Sakaki et al., Chemical Abstracts, vol. 126:212433, 1997.*
Chan et al., Chemical Abstracts, vol. 126:47207, 1996.*

(List continued on next page.)

Primary Examiner—Richard L. Raymond
(74) Attorney, Agent, or Firm—Howrey Simon Arnold & White, LLP

(57) ABSTRACT

The invention relates to non-peptidic compounds that possess bioactive properties, such as the ability to protect neuronal cells from otherwise lethal treatments or the ability to promote the growth or regeneration of neuronal cells. In part, the invention provides compounds that interact with or bind to a cyclophilin and compounds that have activity towards neuronal cells. Methods for using the compounds, such as administering them to cells or animals or using them to treat neurodegenerative conditions, are specifically included.

38 Claims, 10 Drawing Sheets

U.S. PATENT DOCUMENTS

| | | |
|---|---|---|
| 4,957,903 A | 9/1990 | Ranby |
| 4,959,500 A | 9/1990 | Schleifstein |
| 5,003,106 A | 3/1991 | De Vries |
| 5,015,644 A | 5/1991 | Roth |
| 5,015,762 A | 5/1991 | Schirmer |
| 5,019,646 A | 5/1991 | Furcht |
| 5,023,077 A | 6/1991 | Gevas |
| 5,030,653 A | 7/1991 | Trivedi |
| 5,057,610 A | 10/1991 | Pastor |
| 5,059,614 A | 10/1991 | Lepage |
| 5,091,571 A | 2/1992 | Lee |
| 5,099,059 A | 3/1992 | Baker |
| 5,100,899 A | 3/1992 | Calne |
| 5,116,816 A | 5/1992 | Dreyfuss |
| 5,122,511 A | 6/1992 | Dreyfuss |
| 5,130,481 A | 7/1992 | Khanna |
| 5,134,121 A | 7/1992 | Mobley |
| 5,166,429 A | 11/1992 | Ito |
| 5,187,270 A | 2/1993 | Bernatowicz |
| 5,198,582 A | 3/1993 | Oh |
| 5,250,701 A | 10/1993 | Abraham |
| 5,250,717 A | 10/1993 | Knapp |
| 5,273,989 A | 12/1993 | Schwab |
| 5,276,182 A | 1/1994 | Cardin |
| 5,283,362 A | 2/1994 | Hackl |
| 5,284,826 A | 2/1994 | Eberle |
| 5,288,914 A | 2/1994 | Kirchhoff |
| 5,302,742 A | 4/1994 | Landscheidt |
| 5,315,011 A | 5/1994 | Benicewicz |
| 5,321,009 A | 6/1994 | Baeder |
| 5,326,856 A | 7/1994 | Coughlin |
| 5,330,993 A | 7/1994 | Armistead |
| 5,331,004 A | 7/1994 | Denny |
| 5,384,425 A | 1/1995 | Ito |
| 5,414,118 A | 5/1995 | Yosizato |
| 5,432,191 A | 7/1995 | Abraham |
| 5,449,612 A | 9/1995 | Lepargneur |
| 5,449,661 A | 9/1995 | Nakamura |
| 5,451,677 A | 9/1995 | Fisher |
| 5,462,927 A | 10/1995 | Mureau |
| 5,464,820 A | 11/1995 | Burton |
| 5,478,810 A | 12/1995 | Stuber |
| 5,545,719 A | 8/1996 | Shashoua |
| 5,559,150 A | 9/1996 | Soll |
| 5,567,831 A | 10/1996 | Li |
| 5,576,335 A | 11/1996 | Sueda |
| 5,585,518 A | 12/1996 | Marschner |
| 5,612,378 A | 3/1997 | Tianbao |
| 5,614,547 A | 3/1997 | Hamilton |
| 5,614,550 A | 3/1997 | Yoshida |
| 5,621,010 A | 4/1997 | Sueda |
| 5,622,970 A | 4/1997 | Armistead |
| 5,624,894 A | 4/1997 | Bodor |
| 5,624,937 A | 4/1997 | Reel |
| 5,661,182 A | 8/1997 | Abraham |
| 5,696,135 A | 12/1997 | Steiner |
| 5,719,320 A | 2/1998 | Jinbo |
| 5,721,256 A | 2/1998 | Hamilton |
| 5,723,075 A | 3/1998 | Hayasaka |
| 5,728,659 A | 3/1998 | Naka |
| 5,780,484 A | 7/1998 | Zelle |
| 5,786,378 A | 7/1998 | Hamilton |
| 5,795,908 A | 8/1998 | Hamilton |
| 5,798,355 A | 8/1998 | Steiner |
| 5,801,187 A | 9/1998 | Li |
| 5,801,197 A | 9/1998 | Steiner |
| 5,811,434 A | 9/1998 | Zelle |
| 5,840,305 A | 11/1998 | Bukrinsky |
| 5,843,906 A * | 12/1998 | Chandrakumar et al. ..... 514/19 |
| 5,843,960 A | 12/1998 | Steiner |
| 5,846,979 A | 12/1998 | Hamilton |
| 5,846,981 A | 12/1998 | Steiner |
| 5,849,732 A | 12/1998 | Suzuki |
| 5,858,327 A | 1/1999 | Pollak |
| 5,859,031 A | 1/1999 | Hamilton |
| 5,874,449 A | 2/1999 | Hamilton |
| 5,898,029 A | 4/1999 | Lyons |
| 5,945,450 A | 8/1999 | Takenouchi |
| 5,972,924 A | 10/1999 | Keep |
| 5,986,044 A | 11/1999 | Cardin |
| 5,994,398 A | 11/1999 | John |
| 6,005,008 A | 12/1999 | Widdowson |
| 6,028,223 A | 2/2000 | Ruminski |
| 6,030,991 A * | 2/2000 | Chan et al. ................. 514/380 |
| 6,043,284 A | 3/2000 | Arrowsmith |
| 6,054,457 A | 4/2000 | Setoi |
| 6,080,753 A | 6/2000 | Lyons |
| 6,083,986 A | 7/2000 | Castle |
| 6,093,742 A | 7/2000 | Salituro |
| 6,121,323 A | 9/2000 | Merrill |
| 6,133,319 A | 10/2000 | Widdowson |
| 6,177,466 B1 * | 1/2001 | Sakaki et al. ............... 514/538 |
| 6,444,643 B1 | 9/2002 | Steiner |

OTHER PUBLICATIONS

Felix et al., Chemical Abstracts, vol. 93:204202, 1980.*

Kremlev et al., Chemical Abstracts, vol. 77:34101, 1972.*

Desjarlais et al., Chemical Abstracts, vol. 74:53338, 1971.*

Agfonov, et al., Chemical Abstracts V. 109, #15 (1988).

Baetge, E. Edward, et al., "Ne urite Outgrowth in PC12 Cells Deficient in GAP–43," *Neuron*, vol. 6, 21–30, Jan. 1991.

Barinaga, M., "Neurotrophic Factors Enter The Clinic," Science 264:772–774.(1998).

Basi, Guriqbal S., et al., "Primary Structure and Transcriptional Regulation of GAP–43, a Protein Associated with Nerve Growth," *Cell*, vol. 49, 785–791, Jun. 19, 1987.

Beck, Klaus D., et al., "Mesencephalic Dopaminergic Neurons Protected by GDNF from Axotomy–Induced Degeneration in the Adult Brain," Nature, 373 (1995) 339–41.

Benowitz, Larry I., et al., "A Membrane Phosphoprotein Associated with Neural Development, Axonal Regeneration, Phospholipid Metabolism, and Synaptic Plasticity," *TINS*, vol. 10, No. 12, 1987.

Bierer, Barbara E., "Two Distinct Signal Transmission Pathways in T Lymphocytes are Inhibited by Complexes Formed Between an Immunophilin and Either FK506 or Rapamycin," *Proc. Natl. Acad. Sci. USA*, vol. 87, pp. 9231–9235, Dec. 1990.

Bisby, M.A., "Depen dence of GAP43 (B50, F1) Transport on Axonal Regeneration in Rat Dorsal Root Ganglion Neurons," *Brain Research*, 458 (1988) 157–161.

Bixby, John L., "Protein Kinase C Is Involoved in Laminin Stimulation of Neurite Outgrowth," *Neuron* 3(3):287–97 (1989).

Braun, W., Three–Dimensional Structure and Actions of Immunosuppressants and Their Immunophilins, *The FASEB Journal*, vol. 9, Jan. 1995.

Bredt, David S., Nitric Oxide Snthase Regulatory Sites, *J. Biol. Chem.* J. Biol. Chem. 267(16) 10976–81 (1992).

Burkhard, P., et al., The Discovery of Steroids and Other Novel FKBP Inhibitors Using a Molecular Docking Program, *J. Mol. Biol.* (1999) 287, 853–858.

Calvo, Victor, et al., "In terleukin 2 Stimulation of p70 S6 Kinase Acitivity is Inhibited by the Immunosuppressant Rapamycin," *Proc. Natl. Acad. Sci. USA*, vol. 89, pp. 7571–7575, Aug. 1992.

Chong, M.S., et al., "GAP–43 mRNA in Rat Spinal Cord and Dorsal Root Ganglia Neurons: Development Changes and Re–expression Following Peripheral Nerve Injury," *European Journal of Neuroscience*, vol. 4, pp. 83–895, 1992.

Christener, Claudia, et al., Synthesis and Cytotoxic Evaluation of Cycloheximide Derivatives as Potential Inhibors of FKBP12 with Neuroregenerative Properties, *J. Med. Chem.*, 1999, 42, 3615–3622.

Chung, Jongkyeong, et al., "Rapamy cin–FKBP Specifically Blocks Growth–Dependent Activation of and Signaling by the 70 kd S6 Protein Kinases," *Cell*, vol. 69, 1227–1236, Jun. 26, 1992.

Comanita, et al., Chemical Abstracts V. 82, #21 (1975).

Connolly, M.A., et al., GPI 1046 Elicits Neurite Outgrowth of Primary Sensory Neuronal Cultures, *Society of Neuroscience*, Abstract 677.13, vol. 23, 1997.

Constantini, Lauren C., et al., "A Novel Immunophilin Ligand: Distinct Branching Effects on Dopaminergic Neurons in Culture and Neurotrophic Actions after Oral Administration in an Animal Model of Parkinson's Disease," Neurobiology of Disease, 5 (1998) 97–106.

Constantini, Lauren C., et al., "Immunophilin ligands can prevent progressive dopaminergic degeneration in animal models of Parkinson's disease," European Journal of Neuroscience, 13 (2001) 1085–92.

Costantini, L.C., Neuroprotective and Regenerative Effects of Immunophilin Ligands in an Animal Model of Parkinson's Diseas e, *Society for Neuroscience*, vol. 23, 1997.

Dawson, Ted M., et al., "Imm unosuppressant FK506 Enhances Phosphorylationof Nitric Oxide Synthase and Protects Against Glutamate Neurotoxicity," *Proc. Natl. Acad. Sci. USA*, vol. 90, pp. 9808–9812, Nov. 1993.

Dawson, Valina L., et al., "Mechanisms of Nitric Oxide – Mediated Neurotoxicity in Primary Brain Cultures," *The Journal of Neuroscience*, Jun. 1993, 13(6): 2651–2661.

Dawson, Valina L., et al., "Nitric Oxide Mediates Glutamate Neurotoxicity in Primary Cortical Cultures," *Proc. Natl. Acad. Sci. USA*, vol. 88, pp. 6368–6371, Jul. 1991.

DeFranco, Anthony L., "I mmunosuppressants at Work," *Nature*, vol. 352, 754–55, Aug. 29, 1991.

Dragovich, P.S., et al., Structure–Based Design of Novel, Urea–Containing FKBP12 Inhibitors, *Book of Abstracts*, 211th American Chemical Society National Meeting.

Dumont, Francis J., et al., "Distinct Mechanisms of Suppression of Murine T Cell Activation by the Related Macrolides FK–506 and Rapamycin," *The Journal of Immunology*, vol. 144, 251–258, No. 1, Jan. 1, 1990.

Dumont, Francis J. et al., "The Immunosuppressive and Toxic Effects of FK–506 are Mechanistically Related: Pharmacology of a Novel Antagonist of FK–506 and Rapamycin," J. Exp. Med., 1992, 176, 751–760.

Dumont, Francis J., et al., "The I mmunosuppressive Macrolides FK–506 and Rapamycin Act as Reciprocal Antagoinists in Murine T Cells," *The Journal of Immunology*, vol. 144, 1418–1424, No. 4, Feb. 15, 1990.

Eberling, J.L., et al., PET Evidence of Nigral Compensation in the MPTP Primate Model of Parkinson's Diseas e, *Society of Neuroscience*, Abstract 677.14vol. 23, 1997.

Ferrari, Stefano, et al., The Immunosuppressant Rapamycin Induces Inactivation of $p70^{s6k}$ through Dephosphorylation of a Novel Set of Sites, *The Journal of Biological Chemistry*, vol. 268, No. 22, pp. 16091–16094, Aug. 5, 1993.

Fruman, David A., et al., "Calc ineurin phosphatase activity in T lymphocytes is inhibited by FK 506 and cyclosporin A," *Proc. Natl. Acad. Sci. USA* 89 (1992) 3686–3690.

Fujita, Ko, et al., "Regulation of the Differentiation of PC12 Pheochromocytoma Cells," *Environmental Health Perspectives*, vol. 80, pp. 127–142, 1989.

Galat, Andrzej, et al., "A Rapamycin–Selecive 25–kDa Immunophilin," *Biochemistry*, vol. 31, No. 8, 1992.

Galat, Andrzej, Peptidylproline cis–trans–isomerases: Immunophilins, *Eur. J. Biochem.* 216, 689–707 (1993).

Gash, Don M., et al., "Functional recovery in parkinsonian monkeys treated with GDNF," Nature, 380 (1996) 252–255.

Gerlach, M. et al., MPTP Mechanisms of Neurotoxicity and Their Implications for Parkinson's Disease, *European Journal of Pharmacology–Molecular Pharmacology Section*, 208 (1991) 273–286.

Girard, Peggy R., et al., "Pr otein Kinase C and Its 80–Kilodalton Substrate Protein in Neuroblastoma Cell Neurite Outgrowth," *Journal of Neurochemistry*, vol. 54, No. 1, 300–306, 1990.

Gold, B.G., et al., A Nonimmunosuppressant FKBP–12 Ligand Increases Nerve Regeneration, *Experimental Neurology* 147, 269–278 (1997).

Gold, B.G. et al., FKBP Ligands Speed Functional Recovery and Nerve Regeneration in the Rat Sciatic Nerve Following Oral Administration, *Society for Neuroscience*, vol. 23, 1997.

Gold, Bruce G., FK506 and the Role of the Immunophilin FKBP–52 in Nerve Regeneration, *Drug Metabolism Reviews*, 31(3), 649–663 (1999).

Gold, Bruce G., et al., "The Immunosuppressant FK506 Increases Functional Recovery and Nerve Regeneration Following Peripheral Nerve Injury," *Restorative Neurology and Neuroscience*, 6 (1994) 287–296.

Grabowski, et al., Chemical Abstracts V. 127 #17 (1997).

Grafstein, Bernice, et al., "I ntracellular Transport in Neurons," *Physiological Reviews*, vol. 60, No. 4, 1167–1283, Oct. 1980.

Greene, Lloyd A., et al., "E stablishment of a Noradrenergic Clonal Line of Rat Adrenal Pheochromocytoma Cells Which Respond to Nerve Growth Factor," *Proc. Natl. Acad. Sci. USA*, vol. 73, No. 7, pp. 2424–2428, Jul. 1976.

Guo, H. et al., The Novel Small Molecule Immunophilin Ligand PI 1046 Stimulates Cholinergic Reinnervation of Deafferented Hippocampal Regions After Fimbria–Fornix Transection, *Society for Neuroscience*, Abstract 677.12, vol. 23, 1997.

Hamilton, G.S. et al., FKBP12–Binding Domain Analogues of FK506 are Potent, Nonimmunosuppressive Neurotrophic Agents In Vitro and Promote Recovery in a Mouse Model of Parkinson's Diseas e, *Bioorganic & Medicinal Chemistry Letters*, vol. 7, No. 13, pp. 1785–1790, 1997.

Hamilton, G.S., et al., Immunophilins: Beyond Immunosuppression, *Journal of Medicinal Chemistry*, vol. 41, No. 26, Dec. 17, 1998.

Handschumacher, Robert E., et al., "Cyclophilin: A Specific Cytosolic Binding Protein for Cyclosporin A," *Science*, vol. 226:544–546, Nov. 1984.

Harrison, R.K., et al., Substrate Specificities of the Peptidyl Prolyl Cis–Trans Isomerase Activities of Cyclophilin and FK–506 Binding Protein: Evidence for the Existence of a Family of Distinct Enzymes, *Biochemistry*, vol. 29, No. 16, Apr. 24, 1990.

Hashimoto, Seiichi, et al., "Blocka ge of Nerve Growth Factor Action in PC12h Cells by Staurosporine, a Potent Protein Kinase Inhibitor," *Journal of Neurochemistry*, vol. 53, No. 6, 1675–85, 1989.

Hicks, T.P., et al., Alterations in the Form and Magnitude of Striatal Synaptic Plasticity in Slices from 6–OHDA–Lesioned Rats, *Society for Neuroscience*, Abstract 677.11, vol. 23, 1997.

Hoffman, Paul N., "Exp ression of GAP–43, a Rapidly Transported Growth–Associated Protein, and Class II Beta Tubulin, a Slowly Transported Cytoskeletal Protein, are Coordinated in Regenerating Neurons," *The Journal of Neuroscience*, 893–97, Mar. 1989, 9(3).

Holt, D.A., et al., Structure–Activity Studies of Synthetic FKBP Ligands as Peptidyl–Prolyl Isomerase Inhibitors, *Bioorganic & Medicinal Chemistry Letters*, vol. 4, No. 2, pp. 315–320, 1994.

Hsiang, J., et al., "The Effects Of Nerve Growth Factor On The Development Of SeptalCholinergic Neurons In Reaggregate Cell Cultures," Neuroscience, 29 (1989) 209–223.

HSU, Linda, "t he Effect of 12–O–Tetradecanoylphorbol–13–Acetate (TPA) on Axonal Elongation and Fasciculation," *Anatomy and Embryology*, 1989, 179:511–518.

Ito, Akira, et al., "T he Complete Primary Structure of Calcineurin A, A Calmodulin Binding Protein Homologous with Protein Phosphatases 1 and 2A," *Biochemical and Biophysical Research Communications*, vol. 163, No. 3, pp. 1492–1497, 1989.

Ivery, M. T. G. et al., Modeling the Interaction Between FK506 and FKBP12: a Mechanism for Formation of the Calcineurin Inhibitory Complex, *Bioorganic & Medicinal Chemistry*, vol. 5, No. 2, pp. 217–232, 1997.

Jackowski, Andre, Neural Injury Repair: Hope for the Future as Barriers to Effective CNS Regeneration Become Clearer, *British Journal of Neurosurgerye* (1995) 9, 303–317.

Jayaraman, Thottala, et al., "F K506 Binding Protein Associated with the Calcium Release Channel (Ryanodine Receptor)", *The Journal of Biological Chemistry*, vol. 267, No. 14, pp. 9474–9477, May 15, 1992.

Jin, Yong Jiu, et al., "The 25–kDa FK506–binding Protein is Localized in the Nucleus and Associates with Casein Kinase II and Nucleolin," *Proc. Natl. Acad. Sci. USA*, vol. 90, pp. 7769–7773, Aug. 1993.

Jin, Yong–Jiu, et al., "Mo lecular Cloining of a Membrane–Associated Human FK506–and Rapamycin–binding Protein, FKBP–13," *Proc. Natl. Acad. Sci. USA*, vol. 88, pp. 6677–6681, Aug. 1991.

Jin, Yong–Jiu, et al., "Mo lecular Cloning of a 25–kDa High Affinity Rapamycin Binding Protein, FKBP25," *The Journal of Biological Chemistry*, vol. 267, No. 16, pp. 10942–10945, Jun. 5, 1992.

Justice, R.M. et al., The Detection of Proline Isomerase Activity in FK506–Binding Protein by Two–Dimensional $^1$H NMR Exchange Spectroscopy, *Biochemical and Biophysical Research Communications*, vol. 171, No. 1, 1990, pp. 445–450.

Kitamura, Yoshihisa, et al., "Su ppressive Effect of FK–506, A Novel Immunosuppressant, Against MPTP–Induced Dopamine Depletion in the Striatum of Young C57BL/6 Mice," *Journal of Neuroimmunology*, 50 (1994) 221–224.

Klivenyi, P., et al., Neuroprotective Effects of Creatine in a Transgenic Animal Model of Amyotrophic Lateral Sclerosis, *Nature Medicine*, vol. 5, No. 3, Mar. 1999.

Kofron, J.L., et al., Determination of Kinetic Constants for Peptidyl Prolyl Cis–Trans Isomerases by an Improved Spectrophotometric Assay, *Biochemistry* 1991, 30, 6127–6134.

Kuno, Takayoshi, et al., "E vidence for a Second Isoform of the Catalytic Subunit of Calmodulin–Dependent Protein Phosphatase (Calcineurin A)," *Biochemical and Biophysical Research Communications*, vol. 165, No. 3, pp. 1352–1358, 1989.

Kunz, Jeannette, et al., "Ta rget of Rapamycin in Yeast, TOR2, Is an Essential Phosphatidylinositol Kinase Homolog Required for $G_1$ Progression," *Cell*, vol. 73, 585–596, May 7, 1993.

Kuo, Calvin J., "Rapam ycin Selectively Inhibits Inteleukin–2 Activation of p70 S6 Kinase," *Nature*, vol. 358, 70–73, Jul. 2, 1992.

Levi, A., et al., "T he Mode of Action of Nerve Growth Factor in PC12 Cells," *Molecular Neurobiology*, vol. 2, 201–26, 1988.

Li, Linxi, et al., "Neurotrophic Agents Prevent Motoneuron Death Following Sciatic Nerve Section in the Neonatal Mouse," Journal of Neurobiology, 25, 7 (1994) 759–66.

Liang, S., et al., Neuroimmunophilin Ligands Augment Serotonin Fiber Protection Following Lesions with Parachloroamphetamine (PCA), *Society for Neuroscience*, Abstract 677.10, vol. 23, 1997.

Lieberman, A.R., "T he Axon Reaction: A Review of the Principal Features of Perikaryal Responses to Axon Injury," *Int. Rev. Neurobiol.* 14:49–124 (1971).

Lin, Leu–Fen H., et al., "GDNF: A Glial Cell Line–Derived Neurotrophic Factor for Midbrain Dopaminergic Neurons," Science, 260 (1993) 1130–32.

Liu, J., et al., "I nhibition of T Cell Signaling by Immunophilin–Ligand Complexes Correlates with Loss of Calcineurin Phosphatase Activity," *Biochemistry* 1992, 31, 3896–3901.

Liu, Jun, et al., "Calcineurin is a Common Target of Cyclophilin–Cyclosporin A and FKBP–FK506 Complexes," *Cell*, 66(4); 807–815 (1991).

Liu, Yuehueng, et al., "Deph osphorylation of Neuromodulin by Calcineurin," *J. Biol. Chem.* 264(22) 12800–04 (1989).

Lyons, W. Ernest, et al., "Imm unosuppressant FK506 Promotes Neurite Outgrowth in Cultures of PC12 Cells and Sensory Ganglia," *Proc. Natl. Acad. Sci. USA*, vol. 91, pp. 3191–3195, Apr. 1994.

Magal, Ella, et al., "Effects of ciliary neuronotrophic factor on rat spinal cord neurons in vitro: survival and expression of choline acetyltransferase and low–affinity nerve growth factor receptors," Developmental Brain Research Brain Research, 63 (1991) 141–150.

Maki, Noboru, et al., "Complem entary DNA Encloding the Human T–Cell FK506–binding Protein, A Peptidylprolyl cis–trans Isomerase Distinct from Cyclophilin," *Proc. Natl. Acad. Sci. USA*, vol. 87, pp. 5440–5443, Jul. 1990.

Matsuoka, Ichiro, et al., "Ce ll–Type–specific Regulation of Nerve Growth Factor (NGF) Synthesis in Non–Neuronal Cells: Comparison of Schwann Cells with Other Cell Types," *The Journal of Neuroscience*, Oct. 1991, 11(10): 3165–3177.

Mattson, M.P., et al., "I ntracellular Messengers in the Generation and Degeneration of Hippocampal Neuroarchitecture," *Journal of Neuroscience Research*, 21:447–464 (1988).

McKeon, Frank, "Wh en Worlds Collide: Immunosuppressants Meet Protein Phosphatases," *Cell*, vol. 66, 823–826, Sep. 6, 1991.

McMahon, S.B., et al., Peripheral Neuropathies and Neurotrophic Factors: Animal Models and Clinical Perspectives, *Neurobiology* 1995, 5:616–624.

Mehta, Sujata, et al., "Ne urite Outgrowth and Protein Phosphorylation in Chick Embryonic Sensory Ganglia Induced by a Brief Exposure to 12–O–Tetradecanoylphorbol 13–Acetate," *Journal of Neurochemistry*, vol. 60, No. 3, 972–81, 1993.

Meiri, Karina F., et al., "Mo noclonal Antibodies Show That Kinase C. Phosphorylation of GAP–43 during Axonogenesis Is Both Spatially and Temporally Restricted In Vivo," *The Journal of Cell Biology*, vol. 112, No. 5, 991–1005, Mar. 1991.

Morrison, Richard S., et al., "I nhibition of Protein Kinase C Activity Promotes the Neurotrophic Actionof Epidermal and Basic Fibroblast Growth Factors," *Brain Research*, 473 (1988) 141–146.

Munroe, J.E., et al., Aryl Alkyl Ureas as Inhibitors of Influenza Virus, *American Chemical Society*, ed. 218, pt 1 (1999).

Navia, M.A., Rational Design of New Immunosuppressive Drugs, *Transplantation Proceedings*, 31, 1097–1098 (1999).

Phelps, C.H., et al., "Comm entary: Potential Use of Nerve Growth Factor to Treat Alzheimer's Disease," *Neurobiology of Aging*, vol. 10, pp. 205–207, 1989.

PR Newswire, Guilford Pharmaceuticals, Inc., "Guilford Pharmaceuticals Announces Completion of NIL–A Phase II Clinical Trial for Parkinson's Disease, First Clinical Evaluation of Neuroimmunophilin Ligands in Parkinson's Disease," Baltimore, Jul. 25, 2001.

Price, D.J. et al., "Rap amycin–Induced Inhibition of the 70–Kilodalton S6 Protein Kinase," *Science*, vol. 257:973–977, Aug. 1992.

Reinhold, David, et al., "T he Lack of a Role for Protein Kinase C in Neurite Extension and in the Induction of Ornithine Decarboxylase by Nerve Growth Factor in PC12 Cells," *J. Biol. Chem.* 264(6): 3538–44 (1989).

Rosenthal, A., et al., "P rimary Structure and mRNA Localizationof Protein F1, A Growth–Related Protein Kinase C Substrate Associated with Synaptic Plasticity," *The EMBO Journal*, vol. 6, No. 12, pp. 3641–3646, 1987.

Ross, D.T. et al., The Novel Neuroimmunophilin Ligan GPI 1046 Stimulates Morphological, Biochemical, and Behavioral Recovery in the Rat Intranigral 6–OHDA Parkinson's Disease Model, *Society for Neuroscience*, Abstract 677.7, vol. 23, 1997.

Ryba, M., et al., Cyclosporine A Prevents Neurological Deterioration of Patients with SAH—A Preliminary Report, *Acta Neurochir (Wien)* (1991) 112: 25–27.

Saika, Takanori, et al., "E ffects of Nerve Crush and Transection on mRNA Levels for Nerve Growth Factor Receptor in the Rat Facial Motoneurons," *Molecular Brain Research*, 9 (1991) 157–160.

Sauer, H., et al., Functional and Anatomical Consequences of Chronic Treatment with Non–Immunosuppressive Immunophilin Ligands after Striatal 6–Hydroxy–Dopamine Lesions in the Rat, *Society for Neuroscience*, Abstract 677.8, vol. 23, 1997.

Schneider, H., et al., Human Cyclophilin C: Primary Structure, Tissue Distribution, and Determination of Binding Specificity for Cyclosporins, *Biochemistry* 1994, 33, 8218–8224.

Schreiber, Stuart L., "Chem istry and Biology of the Immunophilins and Their Immunosuppressive Ligands," *Science*, vol. 251, 283–287, Jan. 18, 1991.

Schreiber, Stuart L., et al., "The Mechanism of Action of Cyclosporin A and FK506," *Immunology Today*, vol. 13, No. 4, 1992.

Schreyer, David J., et al., "Fate of GAP–43 in Ascending Spinal Axons of DRG Neurons After Peripheral Nerve Injury: Delayed Accumulation and Correlation with Regenerative Potential," *The Journal of Neuroscience*, Dec. 1991, 11(2), 3738–3751.

Sexton, Karen E., et al., Thiourea Inhibitors of 15–Lipoxygenase, *American Chemical Society*, ed. 218, pt. 1 (1999).

Sharkey, John, et al., "Imm unophilins Mediate the Neuroprotective Effects of FK506 in Focal Cerebral Ischaemia," *Nature*, vol. 371, 336–39, Sep. 22, 1994.

Shiga, Y., et al., Cyclosporin A Protects Against Ischemia–Reperfusion Injury in the Brain, *Brain Research* 595 (1992) 145–148.

Shoulson, Ira, Experimental Therapeutics of Neurogenerative Disorders: Unmet Needs, *Science*, vol. 282, Nov. 6, 1998.

Shrine, "NGF Receptors Can be Angels of Death," Bioworld Today, 5:1–2, prior to 1998.

Simon, Ralph, et al., "Human CNTF and related cytokines: effects on DRG neurone survival," Neuroreport, 7, (1995) 153–157.

Skene, J.H. Pate, et al., "Axon ally Transported Proteins Associated with Axon Growth in Rabbit Central and Peripheral Nervous Systems," *The Journal of Cell Biology*, vol. 89, Apr. 1981, 96–103.

Skene, J.H. Pate, et al., "Ch anges in Axonally Transported Proteins During Axon Regeneration in Toad Retinal Ganglion Cells," *The Journal of Cell Biology*, vol. 89, Apr. 1981, 86–95.

Skene, J.H. Pate, "Axon al Growth–Associated Protein," *Ann. Rep. Neurosci.* 1989, 12:127–56.

Snipes, G.J., et al., "Regulation of Specific Neuronal and Non–neuronal Proteins During Development and Following Injury in the Rat Central Nervous System," *Progress in Brain Research*, vol. 71, 155–75, F.J. Seil, E. Herbert and B.M. Carlson (Eds.) prior to 1998.

Snyder, S.H. et al., Immunophilins and the Nervous System, *Nature Medicine*, vol. 1, No. 1, Jan. 1995.

Sommervaille, T., et al., "T ime–Dependent Differences in the Increase in GAP–43 Expression in Dorsal Root Ganglion Cells After Peripheral Axotomy," *Neuroscience*, vol. 45, No. 1, pp. 213–220, 1991.

Spitzfaden, C., et al., Determination of the NMR Solution Structure of the Cyclophilin A–Cyclosporin A Complex, *Journal of Biomolecular* NMR, 4 (1994) 463–482.

Standaert, Robert F., et al., "M olecular Cloning and Overexpression of the Human FK–506–binding Protein FKBP," *Nature*, vol. 346, 671–674, Aug. 16, 1990.

Steiner, J.P., et al., Neurotrophic actions of Nonimmunosuppressive Analogues of Immunosuppressive Drugs FK506, Rapamycin and Cyclosporin A. *Nature Medicine*, vol. 3, No. 4, Apr. 1997.

Steiner, J.P., et al., Neurotrophic Immunopilin Ligands Stimulate Structural and Functional Recovery in Neurodegenerative Animal Models, *Proc. Natl. Acad. Sci. USA*, vol. 94, pp. 2019–2024, Mar. 1997 Neurobiolgy.

Steiner, J.P. et al., The Orally Active Neuroimmunophilin Ligand GPI 1046 Promotes Structural and Functional Recovery in the Mouse MPTP Model of Parkinson's Disease, *Society of Neuroscience*, Abstract 677.6, vol. 23, 1997.

Steiner, Joseph P., et al., "Hig h Brain Densities of the Immunophilin FKBP colocalized with calcineurin," *Nature*, 584–587, vol. 358, Aug. 13, 1992.

Stichel, Christine, et al., Experimental Strategies to Promote Axonal Regeneration After Traumatic Central Nervous System Injury, *Progress in Neurobiology*, vol. 56, pp. 119–148, 1998.

Streit, Wolfgang J., et al., "Res ponse of Endogenous Glial Cells to Motor Neuron Degeneration Induced by Toxic Ricin," *The Journal of Comparative Neurology*, 268:248–263 (1988).

Swanson, Selene K.H., et al., "Cy losporin–mediated inhibition of bovine calcineurin by cyclophilins A and B," *Biochemistry*, vol. 89, pp. 3741–3745, May 1992.

Tai, Ping–Kaung Ku, et al., "Associat ion of a 59–Kilodalton Immunophilin with the Glucocorticoid Receptor Complex," *Science*, vol. 256, 1315–18, May 29, 1992.

Tanaka, T. et al., "Human Leukocyte Cathepsin G. Subsite Mapping with 4–Nitroanilides, Chemical Modification, and Effect of Possible Cofactors," Biochem., 1985, 24, 2040–2047.

Teichner, Angela, et al., "Treatment with Cyclosporine A Promotes Axonal Regeneration in Rats Submitted to Transverse Section of the Spinal Cord," Journal fur Hirnforschung, 34 (1993) 3, 343–349.

Tetzlaff, W., et al., "Axon al Transport and Localization of B–50/GAP–43–like Immunoreacitivty in Regenerating Sciatic and Facial Nervers of the Rat," *The Journal of Neuroscience*, Apr. 1989, 9(4), 1303–1313.

Tetzlaff, Wolfram, et al., "Resp onse of Facial and Rubrospinal Neurons to Axotomy: Changesin mRNA Expression for Cytoskeletal Proteins and GAP–43," *The Journal of Neuroscience*, Aug. 1991, 11(8): 2528–2544.

Thoenen, H., et al., "Physiology of Nerve Growth Factor," *Physiological Reviews*, vol. 60, No. 4, 1284–1335, Oct. 1980.

Timerman, Anthony P., et al., "The Calcium Release Channel of Sarcoplasmic Reticulum is Modulated by FK–506–binding Protein," *The Journal of Bilogical Chemistry*, 268 (31): 22992–9 (1993).

Tindall, Richard S.A., "Imm unointervention with Cyclosporin A in Autoimmune Neurological Disorders," *Journal Autoimmun*. 1992 Apr., 5 Suppl. A: 301–13.

Tomac, A., et al., "Protection and repair of the nigrostriatal dopaminergic system by GDNF in vivo," Nature, 373 (1995) 335–9.

Trupp, Miles, et al., "Peripheral Expression of Biological Activities of GDNF, a New Neurotrophic Factor for Avian and Mammalian Peripheral Neurons," Journal of Cell Biology, 130 (1995) 137–148.

Tuszynski, Mark H., et al., "Nerve Growth Factor Infusion in the Primate Brain Reduces Lesion–Induced Cholinergic Neuronal Degeneration," Journal of Neuroscience, 10, 11(1990) 3604–3614.

Valentine, H.L., et al., The Neuroimmunophilin Ligand of GPI 1046 stimulates Recovery Following Sciatic Nerve Injury, *Society for Neuroscience*, Abstract 677.9. vol. 23, 1997.

Van der Zee, Catherina E.E.M., et al., "E xpression of Growth–Associated Protein B–50 (GAP43) in Dorsal Root Ganglia and Sciatic Nerve During Regenerative Sprouting," *The Journal of Neuroscience*, Oct. 1989, 9(10), 3505–3512.

Verge, V.M.K., et al., "Co rrelation Between GAP43 and Nerve Growth Factor Receptors in Rat Sensory Neurons," *The Journal of Neuroscience*, Mar. 1990, 10(3), 926–934.

Wang, G.T., et al., Synthesis and FKBP Binding of Small Molecule Mimics of the Tricarbonyl Region of FK506, *Bioorganic & Medicinal Chemistry Letters*, vol. 4, No. 9, pp. 1161–1166, 1994.

Wang, M.S., et al., Comparative Dose–Dependence Study of FK506 and Cycolsporin A on the Rate of Axonal Regeneration in the Rat Sciatic Nerve, *The Journal of Pharmacology and Experimental Therapeutics*, vol. 282, No. 2, 1997.

Wiese, U.H., et al., "Dif ferential Expression of Growth–Associated Protein (GAP–43) mRNA in Rat Primary Sensory Neurons After Peripheral Nerve Lesion: A Non–Radioactive In Situ Hybridisation Study," *Brain Res*. 592:141–56 (1992).

Wiley, Ronald G., et al., "Su icide Transport: Destruction of Neurons by Retrograde Transport of Ricin, Abrin, and Modeccin," *Science*, vol. 216:889–890, May 1982.

Williams, Lawrence R., et al., "Continuous infusion of nerve growth factor prevents basal forebrain neuronal death after fimbria fornix transection," Proc. Natl. Acad. Sci., 83, (1986) 9231–9235.

Woolf, C.J., et al., "T he Growth–Associated Protein GAP–43 Appears in Dorsal Root Ganglion Cells and in the Dorsal Horn of the Rat Spinal Cord Following Peripheral Nerve Injury," *Neuroscience* 34(2): 465–78 (1990).

Yankner, Bruce A., et al., "T ransfection of PC12 Cells with the Human GAP–43 Gene: Effects on Neurite Outgrowth and Regeneration," *Molecular Brain Research*, 7 (1990) 39–44.

Yem, Anthony W., et al., "T he Hsp56 Component of Steroid Receptor Complexes Binds to Immobilized FK506 and Shows Homology to FKBP–12 and FKBP–13," *The Journal of Biological Chemistry*, vol. 267, No. 5, pp. 2868–2871, Feb. 15, 1992.

* cited by examiner

Neurite Outgrowth in Adult DRGs

Control          1 uM Compound 7

Neurite Outgrowth in Adult DRGs

Control            1 uM Compound 3

Neurite Outgrowth in Adult DRGs

NON-PEPTIDIC CYCLOPHILIN BINDING COMPOUNDS AND THEIR USE

This application is a Continuation-in-Part application of U.S. patent application Ser. No. 09/392,290, filed Sep. 8, 1999, now abandoned.

This invention relates to the biochemistry of cyclophilin proteins, in particular, compounds which interact with or bind such proteins. Cyclophilins (CyP), which bind cyclosporin A, and FK-506 binding proteins (FKBP), which bind FK-506 and rapamycin, are both subclasses of a group of proteins termed immunophilins. Immunophilins were first identified as proteins that bind to the immunosuppressive drugs cyclosporin A, FK-506, and rapamycin. CyPs and FKBPs can also be separated based on their differing structures.

By studying the binding of test compounds to cyclophilin proteins, the inventors have identified a number of new compounds that effect the growth and health of cells in the nervous system. Building on this initial identification, the inventors developed and utilized screening procedures for rapidly identifying additional, similarly active compounds. These compounds have been specifically tested to show that they protect neuronal cells from otherwise lethal treatments, and/or that they promote the growth or regeneration of neuronal cells. In part, the invention provides compounds that interact with or bind to a cyclophilin and compounds that have activity towards neuronal cells. The compounds can be used in a variety of ways, including therapeutic and research and development applications for a number of diseases associated with neuronal degeneration.

Cyclophilin was first identified as the receptor for cyclosporin A, a potent immunosuppressive drug that is still widely used to prevent immunological rejection of transplanted tissue. The effects of the cyclosporin A:cyclophilin interaction have been well documented. Cyclosporin A binds with a dissociation constant in the range of $10^{-8}$ mol/L, a value representing a relatively high degree of attraction (Handschumacher et al., *Science* 226:544 (1984)). While the present invention is not bound by any particular theory, it appears the complex formed between CyP and cyclosporin A exerts the effects on the organism and cells, which leads to immunosuppression. The complex interacts with the cellular enzyme calcineurin, a calmodulin-dependent phosphatase, and the interaction prevents T cell activation by blocking RNA transcription of the T cell growth factor interleukin 2 (IL-2). (Palacios, *J. Immunol.* 128:337 (1982)). Without IL-2 to cause T cell proliferation, specific T cell populations cannot mount a strong immune response, resulting in immunosuppression.

A number of types of mammalian cyclophilins have been identified and cloned, cyclophilins A, B, C, D, and cyclophilin-40 (Snyder and Sabatini, *Nat. Med.* 1:32–37 (1995); Friedman et al., *Proc. Natl. Acad. Sci.*, 90:6815–6819 (1993)). Cyclophilin A is a 19 kD protein, which is abundantly expressed in a wide variety of cells. Like the other cyclophilins, cyclophilin A binds the immunosuppressive agent cyclosporin A and possesses peptidyl-prolyl cis-trans isomerase (PPIase) and protein folding or "chaperone" activities. PPIase activity catalyzes the conversion of proline residues in a protein from the cis to the trans conformation (Fischer, et al., *Biomed. Biochem. Acta* 43:1101–1112 (1984)). Cyclophilin B possesses an N-terminal signal sequence that directs translocation into the endoplasmic reticulum of the cell. The 23 kD cyclophilin C is found in the cytosol of the cell. Cyclophilin D, at 18 kD, appears to target its actions in the mitochondria. And cyclophilin-40 is a component of the inactivated form of a glucocorticoid receptor.

Immunophilins were discovered because of their interaction with known therapeutic drugs. Thus, knowledge about the interaction between drug and protein spawned a number of drug discovery efforts. Initially, the focus was on identifying new immunosuppressive drugs. A number of facts have influenced the search for improved immunosuppressive drugs. One factor was the importance of proline. The native substrate for the PPIase activity in cells is the amino acid proline in a protein. Cyclophilins A–D all contain a conserved proline binding site. The conversion between the cis and trans forms of proline, which PPIase performs, allows a protein to change shape and fold properly.

However, the first identified ligand for cyclophilins, cyclosporin A, which is a cyclic peptide, does not contain a proline. Both FK-506 and rapamycin, which bind FKBP, are also cyclic non-peptidic macrolide antibiotics. The FKBP proteins also possess PPIase activity, although the FKBPs share no significant sequence homology to CyPs. Since FK-506 is a more potent immunosuppressive compound than cyclosporin A, a number of analogs of FK-506 have been developed. So, the cyclic structure also became an important factor in designing potential new drugs.

Later, therapeutic applications in the nervous system were identified (Lyons et al., *PNAS* 91:3191–3195 (1994)). A number of animal models have proven the effectiveness of FKBP ligands in promoting nerve regeneration and nerve growth. (See, for example, Steiner et al., *PNAS* 94:2019–2024 (1997); Hamilton et al., *Bioorg. Med. Chem. Lett.* 7:1785–1790 (1997); Gold et al., *Experiment. Neurol.* 147:269–278 (1997); and Wang et al., *J. Pharm. Exp. Therap.* 282: 1084–1093 (1997).) However, whether or not ligands specific for CyP possess similar activity in the nervous system has been controversial (Hamilton and Steiner, *J. Med. Chem.* 41:5119–5143 (1998); Gold, *Mol. Neurobiol.* 15:285–306 (1997); and Carreau et al., *Neuropharmacol.* 36:1755–62 (1997)). Earlier published work by some of the inventors showed how compounds with an affinity for the cyclophilin immunophilins can be useful in effecting neuronal activity (PCT published applications WO 97/18828 and WO 98/25950). The work of the present invention further demonstrates that ligands specific for CyP are active in the nervous system and expands on the earlier work by providing additional structural and functional aspects.

Researchers have also noted a functional association of cyclophilin A with the Gag protein of the HIV virus (Thali et al., *Nature* 372:363–365(1994)). This has taken drug development approaches in a new direction (See, for example, U.S. Pat. No. 5,767,069). Many researchers now seek to develop drugs that target the interaction between cyclophilin A and Gag in order to disrupt the HIV life cycle (Sternberg, *BioWorld Today* 7:1 (1996)).

SUMMARY OF THE INVENTION

The invention provides a number of compounds that bind to CyP proteins as well as compounds that are structurally or functionally related to those specifically described and shown. The compounds of this invention preferably do not suppress the immune system and preferably do not possess a biological activity involving binding to a FKBP, i.e., the compounds have an $IC_{50}$ greater than 10 μM towards FKBP. A number of methods for determining the binding to CyPs are presented and so are a number of ways for exploiting the binding through in vitro and in vivo methods and uses.

Preferred compounds function to promote or affect neuronal cell growth or growth of nervous system cells, regenerate damaged or diseased neurons, or protect neurons or neuronal cells from damage. Furthermore, aspects of this disclosure can be used in methods to identify and isolate additional CyP binding compounds or additional uses of the compounds.

The invention also provides a number of uses for these compounds, including uses that comprise the step of allowing the compound to contact an immunophilin protein. A variety of permutations of this method can be devised. In particular, the compounds can be used to affect neuronal cells, either in culture or in an animal. Thus, the compounds can be administered to cells or animals to affect a number of conditions associated with the decline, damage, or degeneration of nervous system cells or function.

In one aspect, this invention provides compounds of Formula I and Formula II, shown and described below.

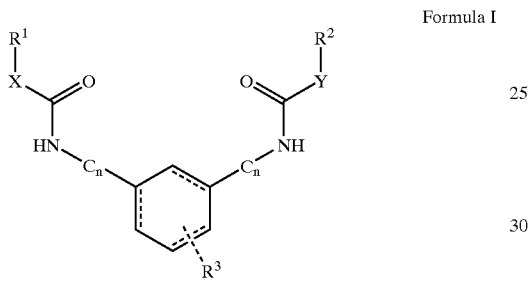

Formula I where n in $C_n$ is 0 or 1;

the dashed bond symbol represents an optional bond;

X and Y may independently be N, NH, O, S, or a direct bond;

$R^1$ is the same or different from $R^2$, and either can be
  one or more C1–C6 branched or straight chain alkyl or alkenyl groups;
  one or more C1–C3 branched or straight chain alkyl groups substituted by one or more Q groups;
  or one or more Q groups,
    where Q, which is optionally saturated, partially saturated, or aromatic, is a mono-, bi-, or tricyclic, carbo- or heterocyclic ring, wherein each ring may be optionally substituted in one to three positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof;

and $R^3$ many be one to three substituents chosen from the group consisting of halo, hydroxyl, nitro, trifluoromethyl, C1–C6 straight or branched chain alkyl or alkenyl, C1–C4 alkoxy, C1–C4 alkenyloxy, phenoxy, benzyloxy, amino, Q as defined above, or a combination thereof.

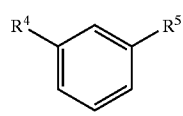

Formula II where $R^4$ and $R^5$ may independently be
  —N—SO$_2$—R,
  —SO$_2$—NRR,
  —O—R,
  —CO—N—R,
  —N—CO—R,
  —CO—R, wherein each R may independently be
  hydrogen, Q, or a C1–C6 branched or straight alkyl or alkenyl chain, which may be substituted in one or more positions by C3–C8 cycloalkyl or cycloalkenyl, hydroxyl, or carbonyl oxygen, and where in said alkyl or alkenyl chain one or more carbon atoms are either optionally substituted with Q, or optionally replaced by O, S, SO, SO$_2$, N, or NH;

where Q, which is optionally saturated, partially saturated, or aromatic, is a mono-, bi-, or tricyclic, carbo- or heterocyclic ring, wherein each ring may be optionally substituted in one to five positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

In a preferred embodiment of a compound of Formula II, each R in $R^4$ and $R^5$ may independently be
  hydrogen, Q, or C1–C6 branched or straight chain alkyl or alkenyl, which may be substituted in one or more positions by C3–C8 cycloalkyl or cycloalkenyl, hydroxyl, carbonyl oxygen, or Q;

where Q, which is optionally aromatic, is a mono-, bi-, or tricyclic, carbo- or heterocyclic ring, wherein each ring may be optionally substituted in one to three positions with halo, hydroxyl, nitro, trifluoromethyl, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

A number of compounds can be selected for use from Formulae I and II. For example, starting with a particular compound, any of the individual variable groups $R^1$–$R^5$, X, Y, and a value for 'n' can be selected while one or more of the other variable groups can be modified. For example, in Formula I, the "n" can be set at 0 to select subgroups of related compounds with X and Y being both NH, or both being O, or X being NH and Y being O, and within each of those 3 groups $R^3$ being present or absent, and then within each of those 6 groups the 6-membered ring structure is either a cyclohexyl or an aromatic ring, which results in 12 subgroups of related compounds. Any of those 12 subgroups can be selected and further divided into additional subgroups of compounds defined by having an $R^1$ the same as $R^2$ or by having both $R^1$ and $R^2$ comprise a substituted benzyl or substituted phenyl group. This process can be repeated using any one or combination of the variable groups. In this way, one skilled in the art can select and use groups of related compounds or even individual compounds, all within the invention. Many examples are shown below; however, they are merely representative of the scope of changes and modifications possible. One skilled in the art can devise many separate compounds from the description of the Formulae alone. Thus, the invention specifically includes numerous individual compounds that fall within the definition of either Formula I or II.

Compounds of Formulae I and II may be prepared or formulated as a salt or derivative for some uses, including pharmaceutical and tissue or cell culture uses. The compounds of the invention can also be part of a composition comprising one or more compounds of Formula I or II. Thus, pharmaceutically acceptable salts and derivatives of any of the compounds, or compositions comprising them, are specifically included in this invention. A compound of Formula I or II, or a compound having Formulae I or II, will optionally include the salt or derivative of the compound depicted in the formula.

The compounds of the invention can be produced as a mixture of isomers or racemic mixtures or as optically pure compounds. Methods for separating stereoisomers can also be used to enrich mixtures for one or more compounds. The compositions of the invention may similarly contain mixtures of stereoisomers, mixtures of one or more stereoisomers, or be enriched for one or more stereoisomers. All of these forms are specifically included in this invention.

Preferably, compounds of Formulae I and II selectively bind to a CyP as detected, for example, by a measurable inhibition of the rotamase (PPIase or peptidyl-prolyl cis-trans isomerase enzyme) activity of CyP. "Selectively bind to a CyP" means the compounds do not possess a significant binding affinity toward a FKBP and/or do not possess a biological activity associated with binding to a FKBP. For example, the $IC_{50}$ towards FKBP is at or above 10 µM or at or above 50 µM. The skilled artisan is familiar with ways to detect rotamase inhibition in CyP and FKBP. In addition, a number of ways for detecting binding to a CyP are described below.

As is readily apparent from Formulae I and II, a common 1-,3-substitution pattern on a central ring structure exists. This common pattern differs from the approaches previously taken to identify other immunophilin binding compounds or drugs. For example, Holt et al. (*Bioorg. Med. Chem. Letters*, 4: 315–320 (1994)) discuss a pipecolate, or 1-(1,2-dioxo)2-carboxylate piperidine containing base structure for binding to FKBP. Similarly, earlier work by the inventors established the relevance of a 1-(1,2-dioxo)2-carboxylate pyrrolidine containing structure for binding to FKBP (Steiner et al., *PNAS* 94:2019–2024 (1997)). Presumably, these structures mimic the natural substrate for the rotamase activity, a proline-containing fragment of a protein. In a protein, the amino acid proline corresponds to a 1,2-substituted pyrrolidine structure. Prior work has generally incorporated that structure. However, Formulae I and II do not correspond to a 1,2- substituted pyrrolidine structure. Yet, as demonstrated here, compounds of these formulae possess important bioactive and biochemical functions.

The body of work related to analogues of cyclosporin A, FK-506, and rapamycin further distances the compounds of this invention from prior work. (See, for example, U.S. Pat. Nos. 5,767,069, 5,284,826, 4,703,033, and 5,122,511.) These analogues typically possess a cyclic peptide structure.

In another aspect, the invention relates to methods for binding non-peptidic compounds to cyclophilin-type immunophilins. Binding results in an "immunophilin:drug" complex, which is considered to be the active agent in the in vivo immunosuppressive and neurotrophic activities of rotamase inhibitors (Hamilton and Steiner, *J. of Med. Chem.* 41:5119–5143 (1998); Gold, *Mol. Neurobiol.* 15:285–306 (1997)). Whether or not the complex acts for any or all the therapeutic actions of these rotamase inhibitors, focusing on the immunophilin:drug interaction has led to the discovery of a number of new drug compounds. Accordingly, methods of using compounds, such as those of Formulae I and II, to create an immunophilin:compound complex, or a CyP:compound complex, provides an important aspect of this invention. This aspect can be exploited, for example, in methods where the compound, or a mixture comprising one or more of the compounds of the invention, is administered to cells in culture or to an animal.

While the immunophilin:compound complex has beneficial effects in vivo and in cultured cells, numerous other uses for binding the compounds to an immunophilin exist. For example, in vitro binding experiments can be used to identify and purify cellular components that interact with the immunophilin complex. An affinity chromatography column or matrix bearing the compound can be reacted with a CyP, and cellular or tissue extracts passed over the column or matrix.

Thus, the invention also provides methods for forming immunophilin:compound or CyP:compound complexes as well as the complexes themselves. To form these complexes, the compounds can contact an immunophilin or CyP protein in vivo, in vitro, or within a cell. In preferred embodiments, the compound contacts a human CyP protein, such as one or more of CyP A, B, C, or D. The CyP protein can be native to the cell or organism, produced via recombinant DNA, produced by other manipulations involving introduced genetic material, or produced by synthetic means. Furthermore, chimeric proteins possessing immunophilin domains that function to bind immunophilin ligands can also be used to form a protein:compound complex. The formation of the CyP:compound, immunophilin:compound, or protein:compound complex need not be irreversible.

The binding of a compound to a CyP can be detected in a number of ways, including rotamase inhibition assay, affinity chromatography, in vivo neuroprotection or neuroregeneration activity assay, in vitro neurotrophic activity assay, or by any of the activities in neuronal cells or cells of the nervous system described below, in the examples, or in the cited references.

The invention also provides compositions comprising at least one compound of Formula I or II. The compositions may comprise one or more pharmaceutically acceptable carriers, excipients, or diluents. These compositions, or the compounds themselves or mixtures of them, can be administered to an animal. Administration can be one method to allow the compound to contact a CyP within the animal. As one skilled in the art would recognize, various routes of administration are possible. Exemplary routes are specifically described in the detailed description below. The compounds of Formulae I and II or compositions comprising them can function to regenerate nerve cells, promote neurite outgrowth, and protect nerves from otherwise damaging treatments or conditions. Thus, the compounds and compositions of this invention can be used to treat animals, including humans, with neurodegenerative conditions or animals exposed to degenerative agents or having damaged nervous system cells.

The following detailed description should not be taken as a limitation on the scope of the invention. The embodiments and examples given are illustrative of the invention. Additional aspects of the invention can be devised by reference to this disclosure as a whole in combination with the references cited and listed throughout and at the end of the specification and the knowledge of one skilled in the art. All of the references cited and listed can be relied on, in their entirety, to allow one to make and use these additional aspects of the invention.

BRIEF DESCRIPTION OF THE DRAWINGS

For each of FIGS. 1–7, the bar graphs represent the number of viable neurons after a specified treatment regimen employed in a neuroprotective activity assay. The cells of the experiments were treated with a control solution, a neurotoxic solution, and neurotoxic+experimental compound solution. The statistical significance, p, is calculated using the standard 2 tailed Student's t test.

Figure 1:
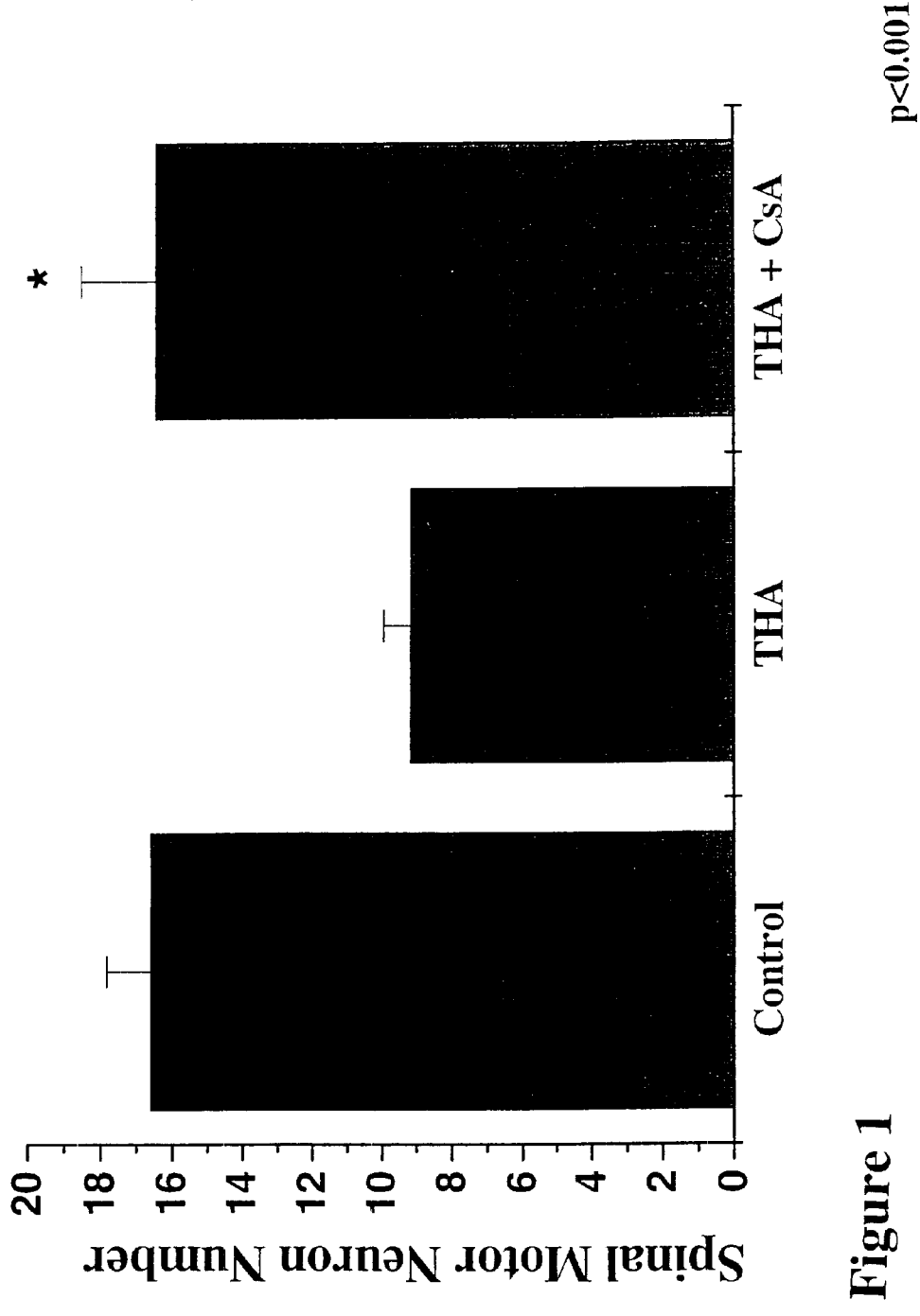
FIG. 1: Primary cultures of spinal motor neurons were treated with control (vehicle), THA neurotoxin, and THA+ cyclopsporin A (CsA), as detailed in the examples. The results show that CsA treatment maintains neuronal viability, which indicates neuroprotective activity.
Figure 2:
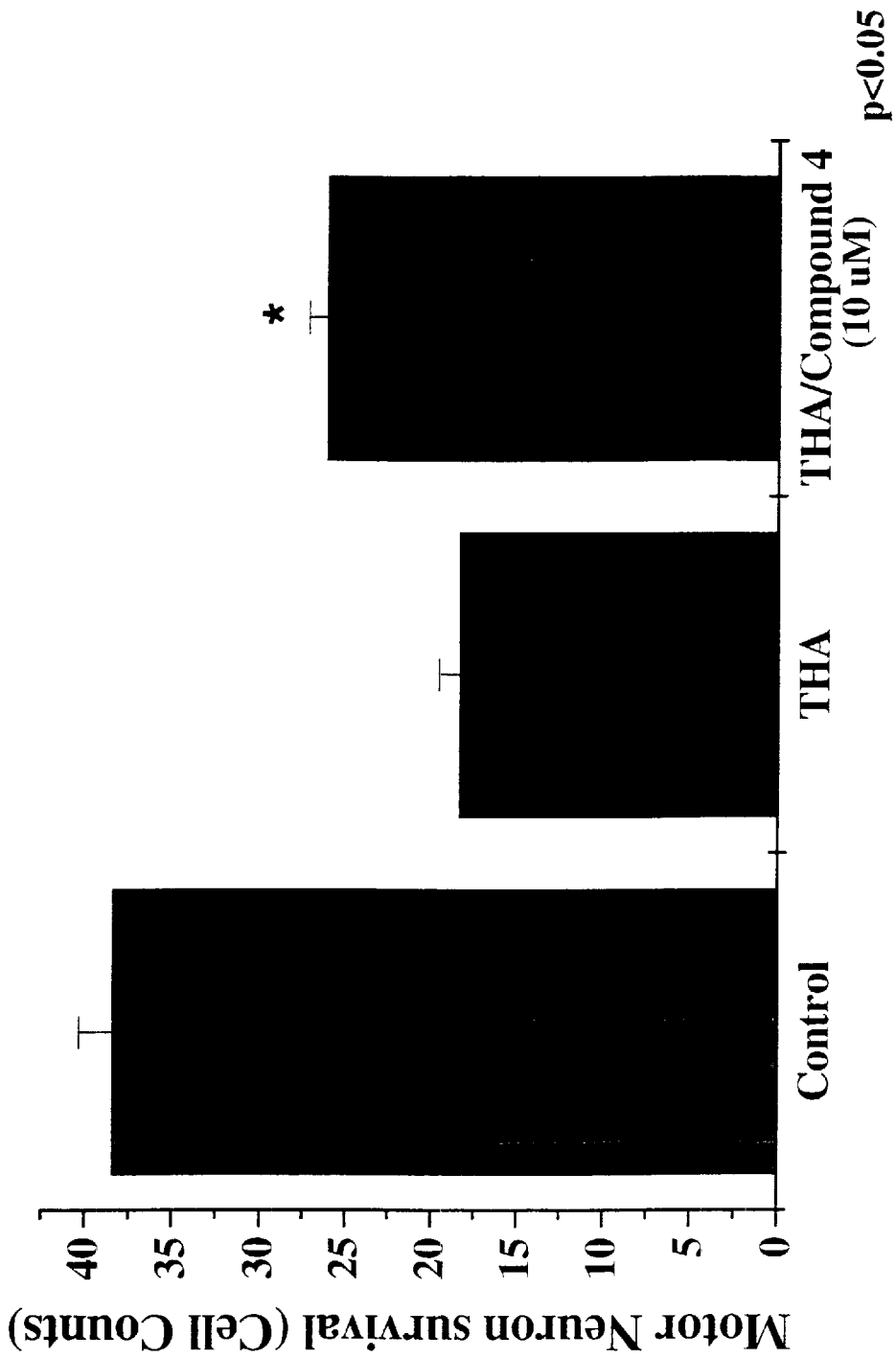
FIG. 2: An experiment as discussed in FIG. 1, where compound #4 was used. Compound #4 also displays neuroprotective activity.
Figure 3:
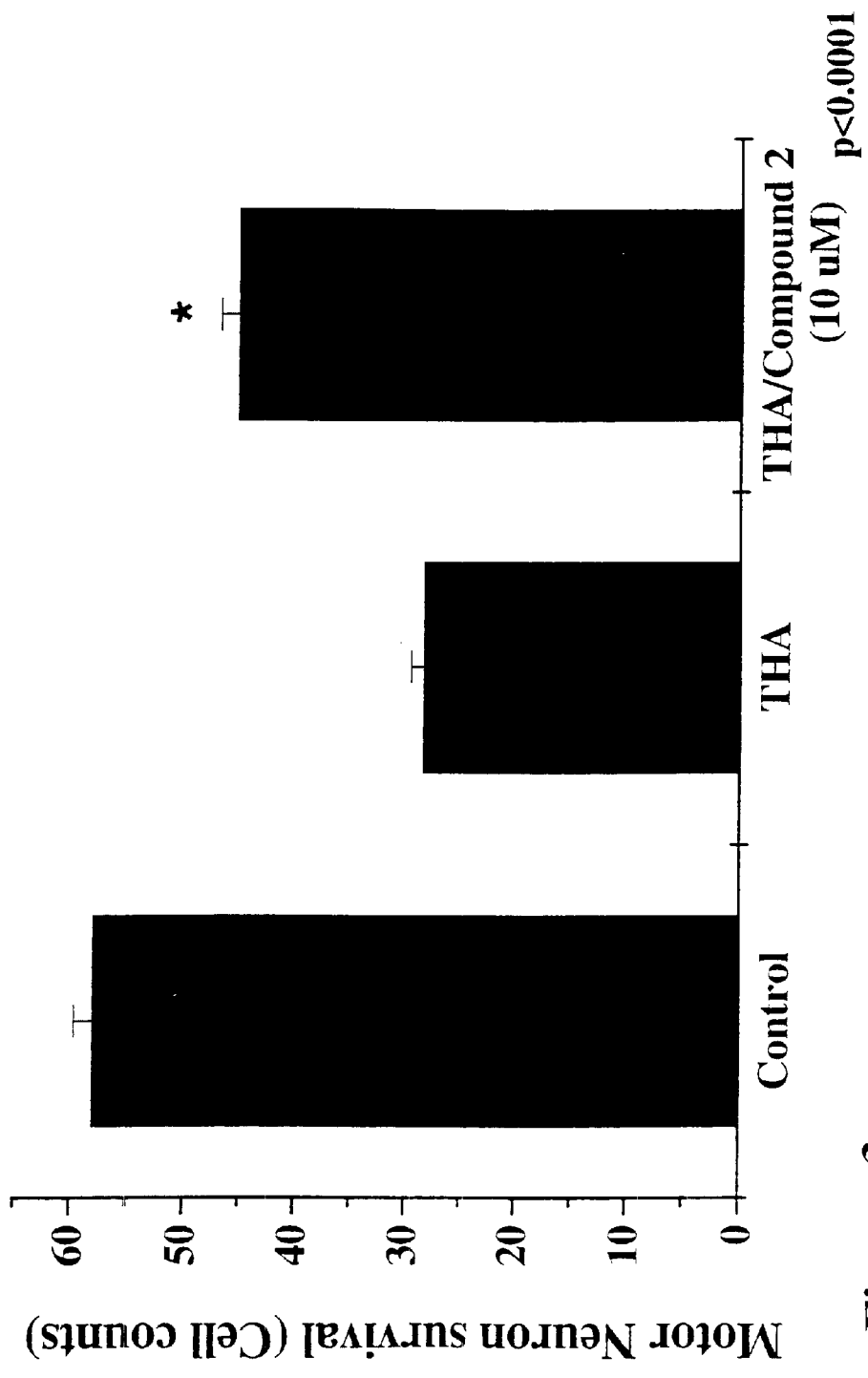
FIG. 3: An experiment as discussed in FIG. 1, where compound #2 was used. Compound #2 also displays neuroprotective activity.
Figure 4:
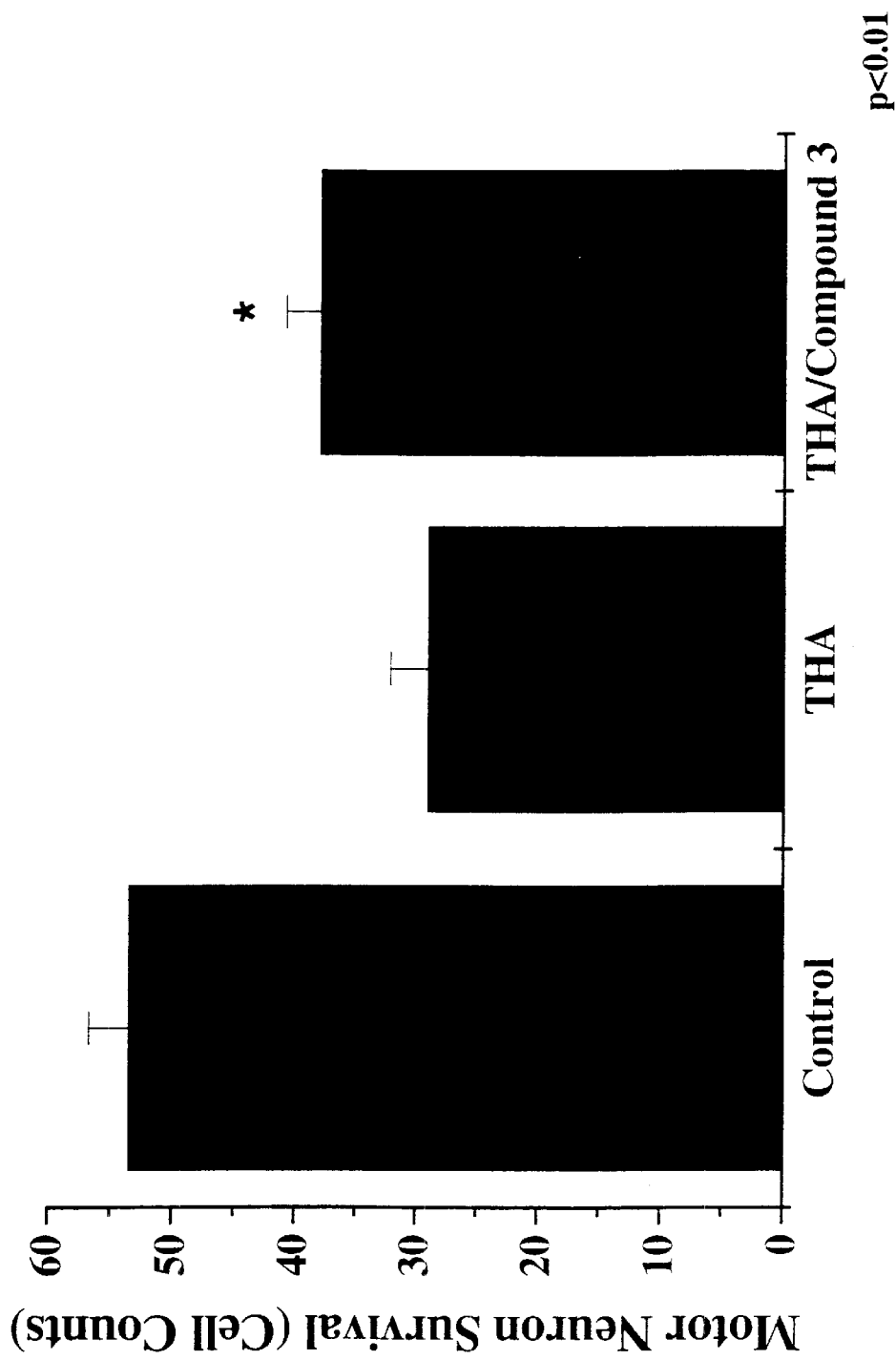
FIG. 4: An experiment as discussed in FIG. 1, where compound #3 was used. Compound #3 also displays neuroprotective activity.
Figure 5:
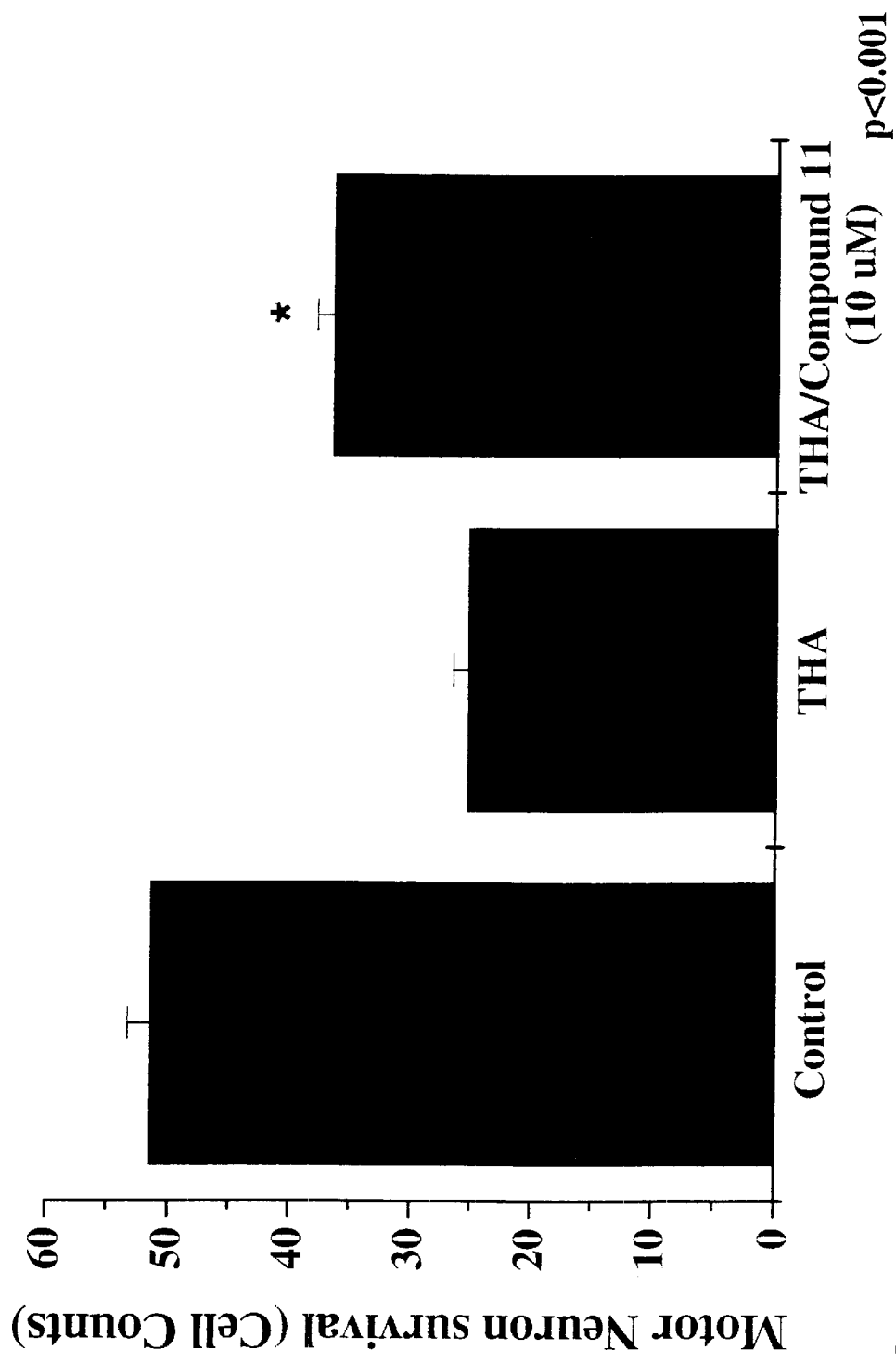
FIG. 5: An experiment as discussed in FIG. 1, where compound #11 was used. Compound #11 also displays neuroprotective activity.
Figure 6:
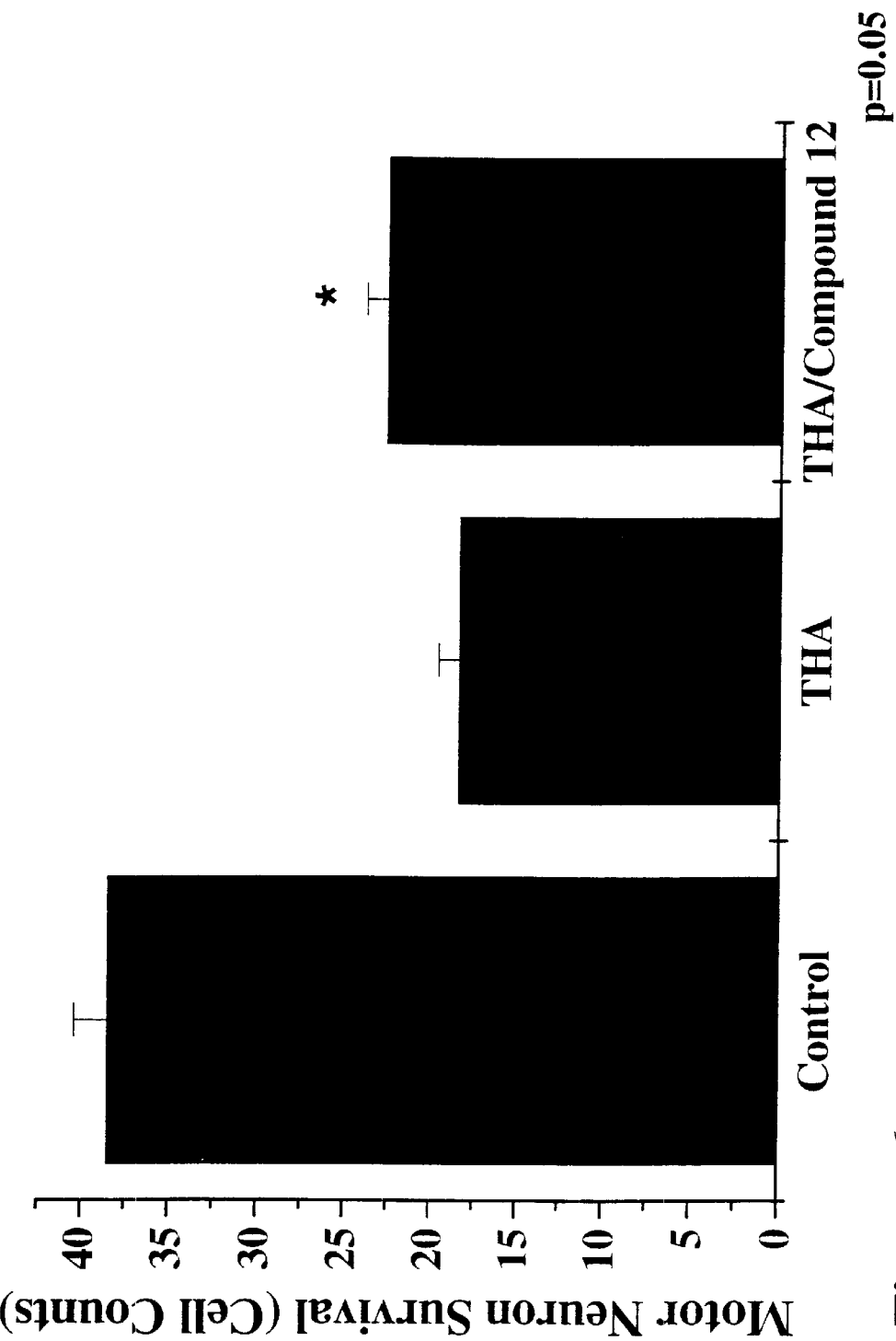
FIG. 6: An experiment as discussed in FIG. 1, where compound #12 was used. Compound #12 also displays neuroprotective activity.
Figure 7:
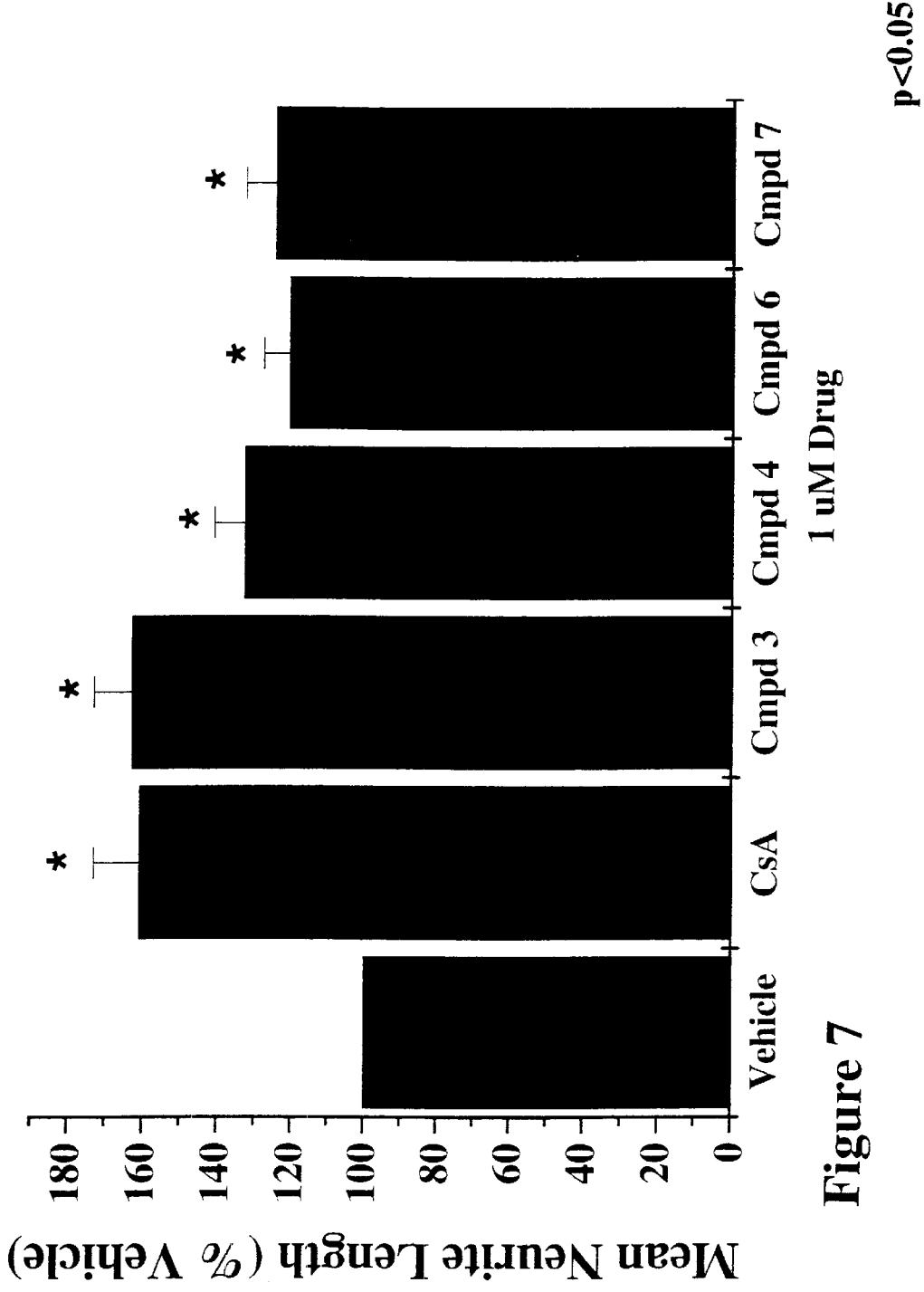
FIG. 7: Primary DRG cultures were used to test for neurotrophic, neurite outgrowth promoting, and neuroregenerative activity. Each of the compounds was incubated with cells at a concentration of 1 μM for 48 hours, as detailed in the examples. The results show the average length of neurites after treatment as a percent of control (vehicle). All of the compounds tested demonstrate neurotrophic activity.
Figure 8:
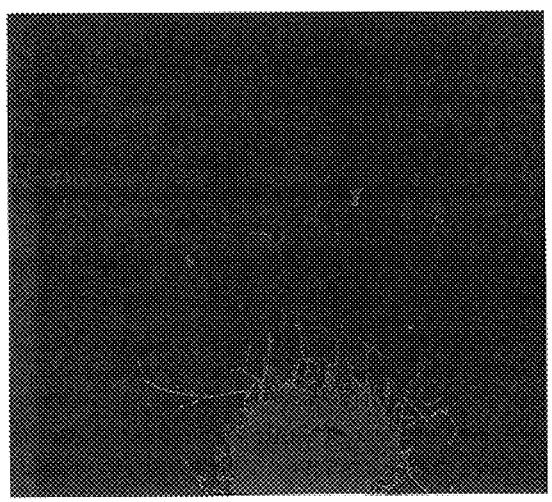
Figure 8:
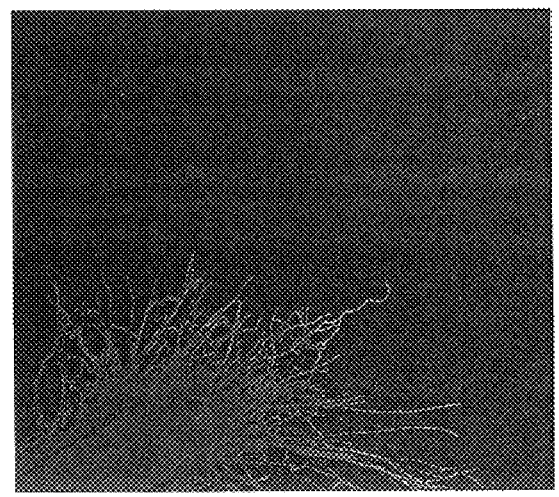
Figure 9:
Figure 9:
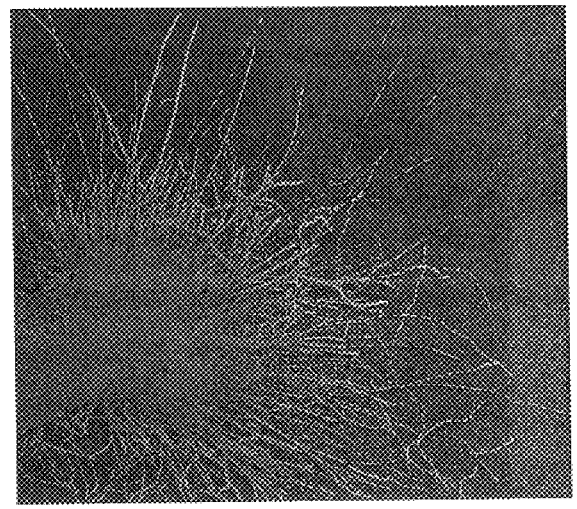
Figure 10:
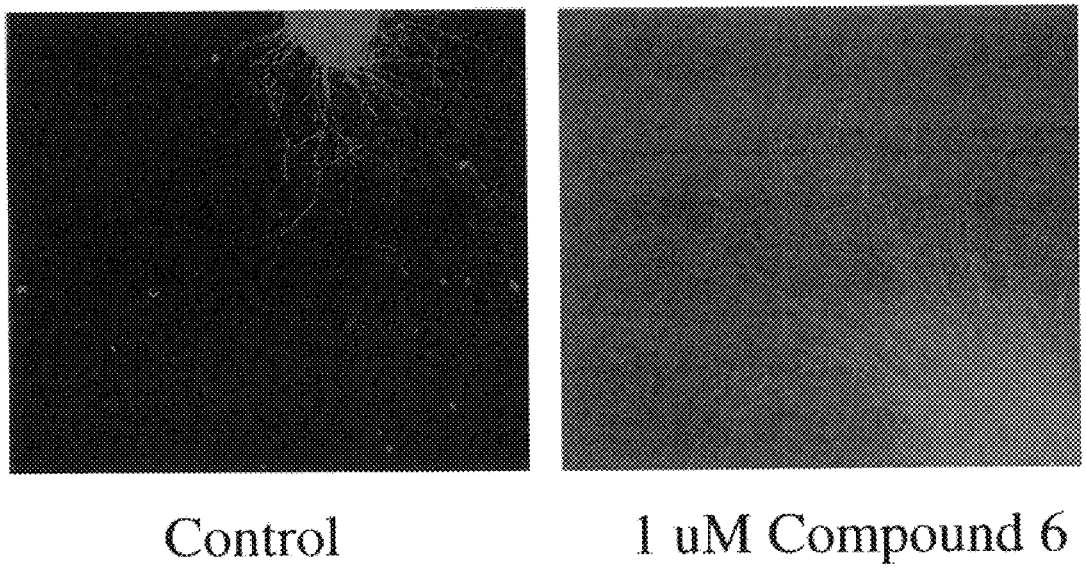

For each of FIGS. 8–10, the images depict the state of neurite outgrowth following a specific treatment regimen and a comparison to control.

FIG. 8: Images depicting representative increase in neuronal cell growth/neurite extension, following treatment with compound #7.

FIG. 9: Images depicting representative increase in neuronal cell growth/neurite extension, following treatment with compound #3.

FIG. 10: Images depicting representative increase in neuronal cell growth/neurite extension, following treatment with compound #6.

DETAILED DESCRIPTION OF EXEMPLARY EMBODIMENTS

One skilled in the art can refer to general reference texts for detailed descriptions of known techniques discussed herein or equivalent techniques. These texts include *Current Protocols in Molecular Biology* (Ausubel, et al., eds., John Wiley & Sons, N.Y., and supplements through June 1999), *Current Protocols in Immunology* (Coligan, et al., eds., John Wiley and Sons, N.Y., and supplements through June 1999), and *Current Protocols in Pharmacology* (Enna et al., eds., John Wiley & Sons, N.Y., and supplements through June 1999) for example, each of which are specifically incorporated by reference in their entirety. These texts can also be referred to in making or using an aspect of the invention.

As noted above, cyclosporin A was the first compound identified to bind a CyP. Based on the cyclic structure of cyclosporin A, a number of large, usually cyclic peptides were developed as immunosuppressive compounds that bind CyP. Now, unexpectedly, the inventors have found a non-peptidic class of CyP binding compounds with activity in neuronal cells.

The following compounds are representative of those tested.

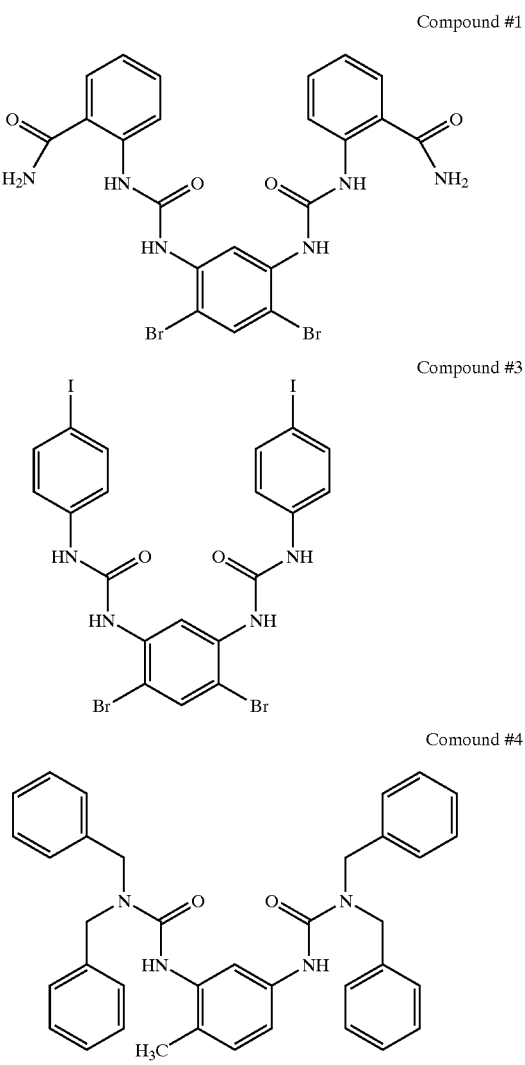

-continued
Compound #6
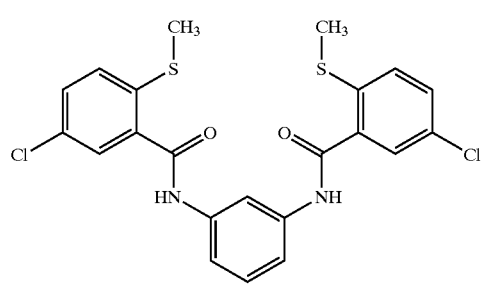
Compound #7
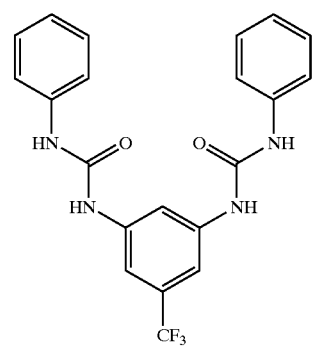
Compound #9
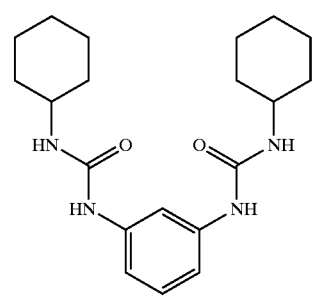
Compound #10
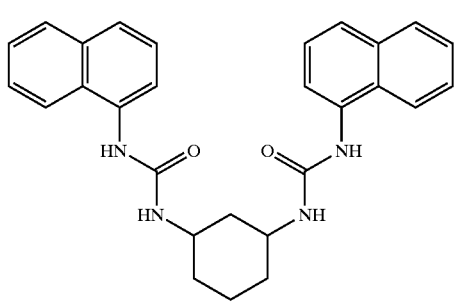
Compound #21
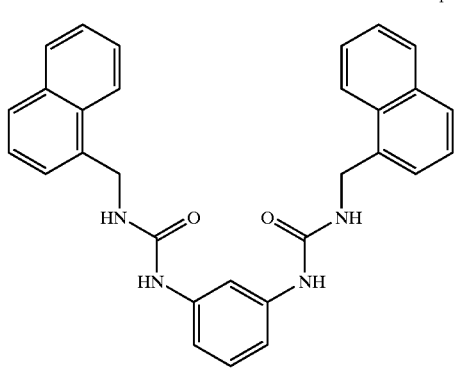
-continued
Compound #22
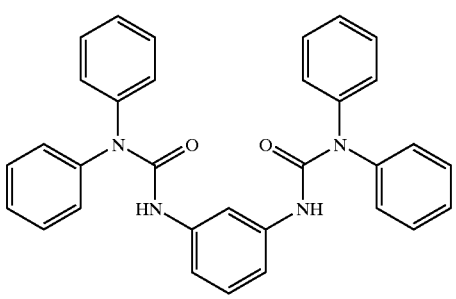
Compound #23
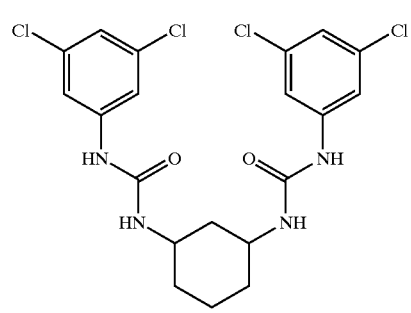
Compound #24
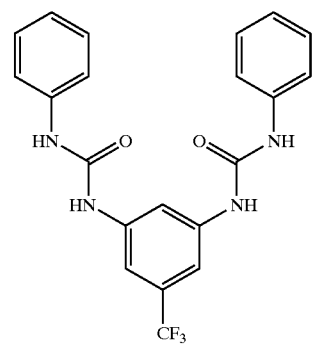
Compound #25
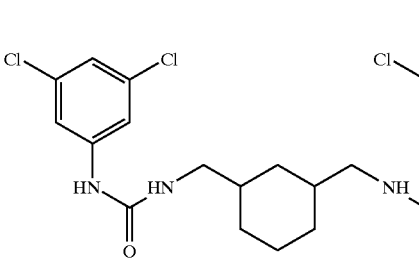
Compound #26
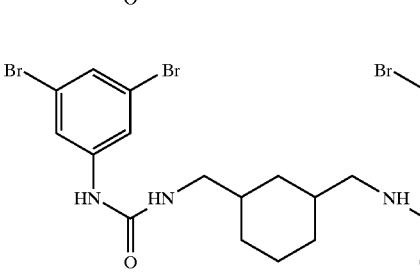

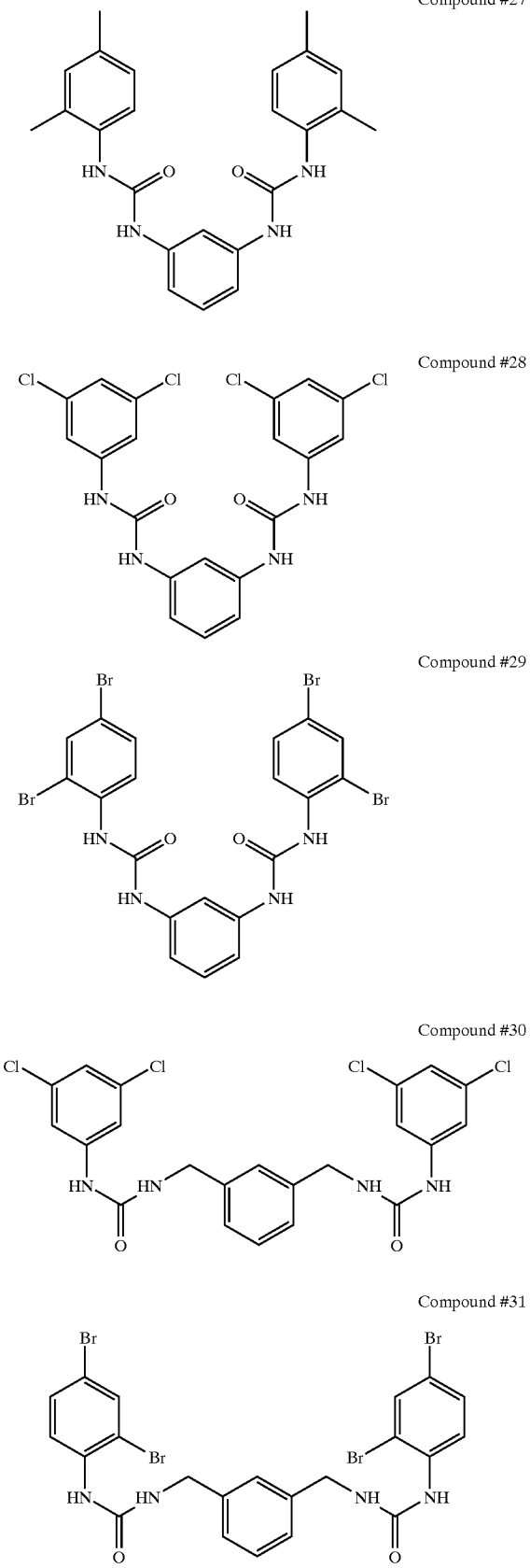

Compound #27

Compound #28

Compound #29

Compound #30

Compound #31

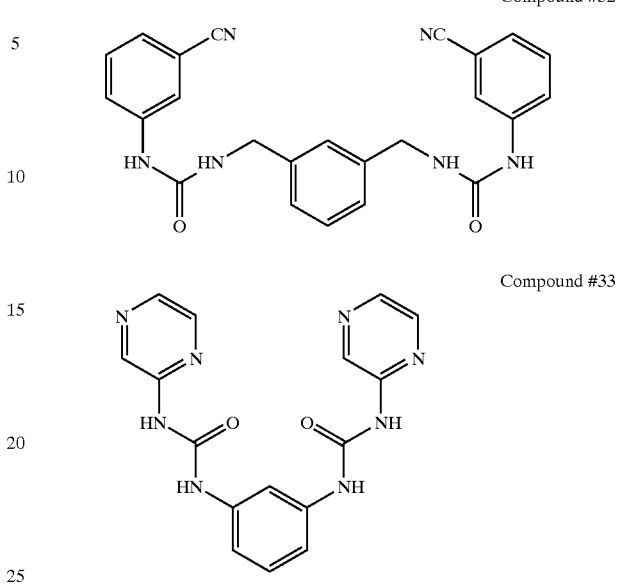

Compound #32

Compound #33

Each of compounds 1–4, 6, 7, and 10–31 significantly inhibit cyclophilin rotamase activity at a concentration of 10 μM or below, and many inhibit 50% of cyclophilin rotamase activity at a concentration lower than 5 μM (IC$_{50}$), some lower than 1 uM. Compounds 6 and 7 possess neurotrophic or neuroprotectant activity.

These data demonstrate the broad range of possibilities for a number of structural elements in the compounds of the invention. Indeed, a number of substituents are well tolerated. Accordingly, the scope of the invention is not limited to those compounds specifically described by Formulae I and II and those depicted in this specification. By performing any one or more of the assays for detecting CyP binding, one skilled in the art can determine whether or not modifications to the R$^{1-5}$ groups, X or Y groups, or the value of n for Formulae I and II, result in a CyP binding compound of this invention.

Preparation of Compounds of the Invention

The compounds of the invention can be prepared by a number of synthetic routes. The examples below detail schemes 1 to 4 and the preparation of specific compounds. However, one skilled in the art can modify the steps, reactants, and reaction conditions in the examples and schemes to arrive at numerous examples of compounds of the invention. In addition, if particular stereoisomers or mixtures are desired, the starting materials and/or reactants in the preparatory scheme can be selected and used accordingly. Alternatively or in addition, particular intermediates can be purified or enriched by chromatographic or enzymatic methods, or by manipulating reaction conditions or selective crystallization, to generate particular final products or mixtures. One skilled in the art is familiar with numerous methods to selectively produce or enrich for desired stereoisomers or mixtures. All of the compounds of the examples, including the intermediates, are specifically included in the compounds of the invention and can be used in the methods of the invention.

The compounds of the invention may be prepared as a salt or derivative. Various salts and derivatives are known in the art and a non-limiting list of possible choices includes acid salts: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, mesylate, dimesylate, pamoate, pectinate, persulfate, 3-phenylpropionate, phosphates, picrate, pivalate, propionate, succinate, sulfates, tartrate, thiocyanate, tosylate, and undecanoate. Base salts may include: amine salts, ammonium salts, alkali metal salts such as sodium and potassium salts, alkaline earth metal salts such as calcium and magnesium salts, salts with organic bases such as dicyclohexylamine salts, N-methyl-D-glucosamine, and salts with amino acids, for example arginine or lysine. Nitrogen-containing groups of the compound can be quaternized with agents as: alkyl halides, for example methyl, ethyl, propyl, and butyl chlorides, bromides, or iodides; dialkyl sulfates, for example dimethyl, diethyl, dibutyl and diamyl sulfates, long chain halides, for example decyl, dodecly, lauryl, myristyl, or stearyl chlorides, bromides, or iodides; and aralkyl halides, for example benzyl and phenethyl bromides, chlorides, or iodides. The skilled artisan is familiar with methods for producing and testing any suitable salt or derivative. (See, for example, *Remington's Pharmaceutical Sciences*, Mack Publishing Co., Easton, Pa., 18$^{th}$ Edition, specifically incorporated herein by reference.)

Activity in Neuronal or Nervous System Cells

In general, activity in the nervous system for a particular compound can be identified by assaying for the ability to promote neurite outgrowth, protect neurons from damage by chemical treatments, promote the growth of neurons or neuronal cells, recover lost or damaged motor, functional or cognitive ability associated with nervous tissue or organs of the nervous system, or regenerate neurons. These activities can be useful in treating, diagnosing, or prognosing a number of human disease conditions, including, but not limited to, Parkinson's disease, Alzheimer's disease, amyotrophic lateral sclerosis (ALS), traumatic injury, spinal cord injury, multiple sclerosis, diabetic neuropathy, neuropathy associated with medical treatments such as chemotherapy, ischemia or ischemia-induced injury, stroke, oxygen deprivation, retinopathies, peripheral neuropathies, and neuropathies associated with viral infection.

A number of animal model assays and cell culture assays have been developed and can be relied on for their clinical relevance to disease treatments, including the human diseases noted above. Each of the following references can be used as a source for these assays, and all of them are specifically incorporated herein by reference in their entirety for that purpose: Steiner, et al., *PNAS* 94: 2019–2024 (1997); Hamilton, et al., *Bioorgan. Med.Chem.Lett.* 7:1785–1790 (1997); McMahon, et al., *Curr. Opin. Neurobiol.* 5:616–624 (1995); Gash, et al., *Nature* 380:252–255 (1996); Gerlach, et al., *Eur. J. Pharmacol.-Mol. Pharmacol.* 208:273–286 (1991); Apfel, et al., *Brain Res.* 634:7–12 (1994); Wang, et al., *J. Pharmacol. Exp. Therap.* 282:1084–1093 (1997); Gold, et al., *Exp. Neurol.* 147:269–278 (1997); Hoffer et al., *J. Neural Transm.* [*Suppl.*] 49:1–10 (1997); and Lyons, et al., *PNAS* 91:3191–3195 (1994).

Preferred methods for detecting neuronal activity include a neuroprotective assay, in which a compound is tested for the ability to protect against treatment causing glutamate neurotoxicity. Sensory neuronal cultures (DRG) can also be assayed for neurite outgrowth, an assay for neurotrophic activity. Cultured cells are treated with a compound of the invention and later assayed for the presence of new neurite fibers. Immunohistochemistry can aid in the visualization and quantitation of neurites as compared to control.

The compounds of the invention can also be used to promote the establishment or maintenance of tissue or cell cultures. Similar to the use for promoting neuronal cell growth, the compounds can be added to primary, transformed, or established cell cultures. Particularly in the case of neuronal cells, the compounds can induce growth in culture and extend the culture lifetime of cells.

Binding to CyP and Other Uses

In addition to or in the alternative to the activity in neuronal or nervous system cells, the compounds of the invention bind CyP. A recognized method for assessing the affinity of the compound to cyclophilin is the rotamase inhibition assay. For this purpose, the following references are specifically incorporated by reference and can be relied on to make assays of rotamase inhibition: Fischer, et al., *Biomed. Biochem. Acta* 43:1101–1112 (1984); Kofron, et al., *Biochem.* 30:6127–6134 (1991); Kofron et al., *J. Am. Chem. Soc.* 114:2670–2675 (1992); Harrison et al., *Biochem.* 29:3813–3816 (1990); Lang et al., *Nature* 329:268–270 (1987); Mucke et al., *Biochem.* 31:7848–7854 (1992); Schonbrunner et al., *J. Biol. Chem.* 266:3630–3635 (1991); Hsu et al., *J. Am. Chem. Soc.* 112:6745–6747 (1990); and Justice et al., *Biochem. Biophys. Res. Commun.* 171:445–450 (1990).

Additional uses for the compounds, which may or may not relate to CyP binding, are also included in the methods of the invention. For example, the compounds may be used to promote hair growth (see, for example, Maurer, et al. *Am. J. Pathol.* 150(4): 143–341 (1997)). The compounds may also be used to treat or effect mitochondrial disorders, metabolic disorders, diabetes, or vision loss. Also, the compounds can be used to treat viral infections, such as with an HIV virus or influenza virus.

Pharmaceutical Formulations and Routes of Administration

The compounds of the invention have utility in pharmacological compositions for the treatment and prevention of various neurodegenerative conditions or for various in vitro and cell culture treatments. The compounds may also have utility in pharmacological compositions for the treatment and prevention of HIV-infection, promotion of hair growth, immunosuppression, mitochondrial disorders, traumatic injury to nervous tissue, or conditions associated with optic nerve damage. The compounds of the invention may be prepared as a salt or derivative, as described above.

A compound of the invention can be administered to an animal or human patient by itself or in pharmaceutical compositions where it is mixed with suitable carriers or excipients, at doses to treat or ameliorate various conditions. A therapeutically effective dose refers to that amount of the compound sufficient to effect an activity in a nerve or neuronal cell, or produce a detectable change in a cell or organism. Therapeutically effective doses may be administered alone or as adjunctive therapy in combination with other treatments for HIV infection or associated diseases. Techniques for the formulation and administration of the compounds of the instant application may be found in *Remington's Pharmaceutical Sciences*, Mack Publishing Co., Easton, Pa., 18$^{th}$ edition (1990).

Suitable routes of administration may, for example, include oral, rectal, transmucosal, buccal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the agent of the present invention in a targeted drug delivery system, for example in a liposome coated with an antibody. The liposomes will be targeted to and taken up selectively by cells expressing the appropriate antigen.

The pharmaceutical compositions of the present invention may be manufactured in a manner that is itself known, e.g., by means of conventional mixing, dissolving, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries, which facilitate processing of the active compounds into preparations, which can thus be used pharmaceutically.

For injection, the agents of the invention may be formulated in aqueous solutions, preferably in physiologically compatible buffers, such as Hank's solution, Ringer's solution, or physiological saline buffer. For transmucosal or buccal administration, penetrants appropriate to the barrier to be permeated may be used in the formulation. Such penetrants are known in the art.

For oral administration, the compounds can be formulated readily by combining the active compounds with pharmaceutically acceptable carriers, well known to those in the art. Such carriers enable the compounds of the invention to be formulated as tablets, pills, capsules, liquids, quick-dissolving preparations, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

In general, the pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. If desired, disintegrating agents may be added, such as the cross-linked polyvinyl pyrrolidone, agar, or alginic acid or a salt thereof such as sodium alginate or a number of others disintegrants (see, for example, *Remington's Pharmaceutical Sciences*, Mack Publishing Co., Easton, Pa., 18$^{th}$ edition (1990)).

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, pressurized air, or other suitable gas or mixture. In the case of a pressurized aerosol the dosage unit may be determined by providing a valve to deliver a metered amount. Capsules and cartridges of e.g. gelatin for use in an inhaler or insulator may be formulated containing a powder mix of the compound and a suitable powder base such as lactose or starch.

The compounds may be formulated for parenteral administration by injection, e.g., by bolus injection or continuous infusion. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization may be employed.

Pharmaceutical compositions suitable for use in the present invention include compositions wherein the active ingredients are contained in an effective amount to achieve their intended purpose, to effect a therapeutic benefit, or to effect a detectable change in the function of a cell, tissue, or organ. More specifically, a therapeutically effective amount means an amount effective to prevent the development of or to alleviate the existing symptoms of the subject being treated. Determining the effective amount is well within the capability of those skilled in the art, especially in light of the detailed disclosure provided herein.

Toxicity and therapeutic efficacy of the compounds or compositions can be determined by standard pharmaceutical, pharmacological, and toxicological procedures in cell cultures or experimental animals. For example, numerous methods for determining the $LD_{50}$ (the dose lethal to 50% of the population) and the $ED_{50}$ (the dose therapeutically effective in 50% of the population) exist. The dose ratio between toxic and therapeutic effects is the therapeutic index, which can be expressed as the ratio between $LD_{50}$ and $ED_{50}$. Compounds and compositions exhibiting high therapeutic indices are preferred. The data obtained from cell culture assays or animal studies can be used in formulating a range of dosages for use in humans. (See, for example, Fingl et al., in *The Pharmacological Basis of Therapeutics*, Ch. 1 p. 1 (1975).)

ILLUSTRATIVE EXAMPLES

Synthetic Routes to Production of Exemplary Compounds of the Invention

A subset of the compounds of Formula I may be prepared by reacting isocyanates with amines, as depicted in Scheme 1 below.

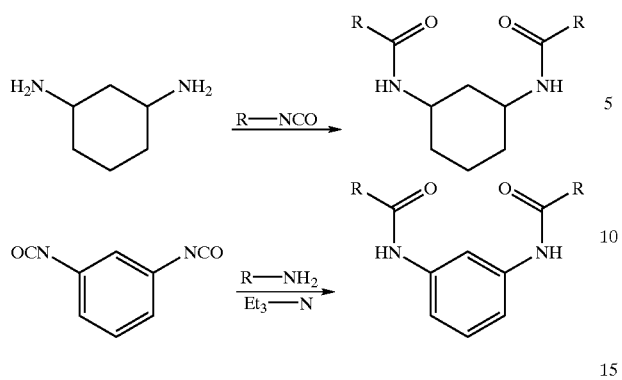

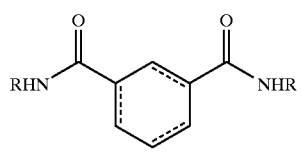

One skilled in the art is familiar with suitable reaction conditions and parameters. The synthesis of compound 9, detailed below, illustrates.

One skilled in the art is familiar with suitable reaction conditions and parameters. The synthesis of compound 14, detailed below, illustrates.

Compound #9

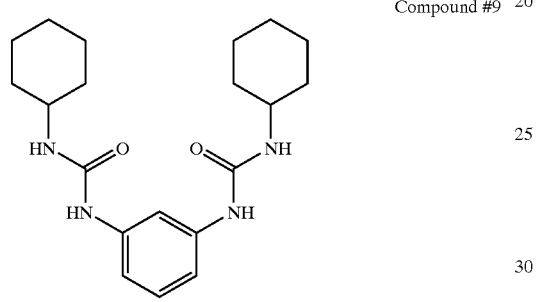

Compound #14

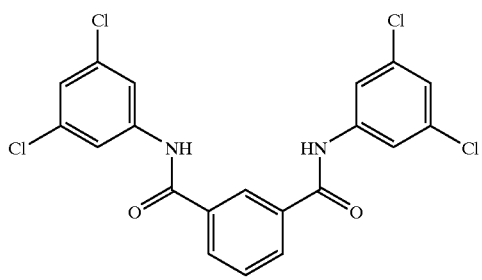

A mixture of phenyl-1,3-diisocyanate (0.1 mmol), cyclohexylamine (0.25 mmol), and diisopropylethylamine (0.1 mmol) in 1 ml dichloromethane was stirred overnight. The resulting precipitate was washed with water and ether to provide (cyclohexylamino)-N-{3-[(cyclohexylamino)carbonylamino]phenyl}formamide (GPI 7104) as a white solid, having $^1$H NMR (CDCl$_3$, 400 MHz) peaks as follows: δ0.88(m, 6H); 1.07(m, 4H); 1.28(m, 2H); 1.41(m, 4H); 1.59(m, 4H); 6.73(m, 3H); 7.17(s, 1H); 7.52(m, 3H); 7.78 (m, 1H).

Another subset of compounds of Formula I may be prepared by the route depicted in Scheme 2 below.

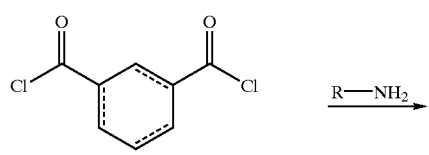

A solution of 1,3-bis-benzoyl chloride (0.99 g, 4.9 mmol), 3,5-dichloroaniline (1.58 g, 9.75 mmol), and triethylamine (2 ml, 14.3 mmol) in 50 ml of dichloromethane was stirred at room temperature overnight. The reaction mixture was washed with water and the resulting precipitated solid was collected by filtration to deliver 1.94 g of crude solid. Recrystallization from acetone furnished analytically pure material with a Mp=260–262° C. and $^1$H NMR (DMSO, 400 MHz) peaks at: δ7.37 (m, 2H); 7.76 (t, 1H, J=7.8); 7.93 (d, 4H, J=1.8); 8.18 (dd, 2H, J=1.7, 7.8); 8.52 (d, 1H, J=1.5); 10.73 (s, 2H). The theoretical atomic composition for C$_{20}$H$_{12}$N$_2$O$_2$Cl$_4$ [C, 52.90; H, 2.66; N, 6.17; Cl, 31.23], compares favorably with that found experimentally [C, 53.04; H, 2.72; N, 6.11; Cl, 31.35].

A subset of the compounds of the invention with unsymmetrical substituents off of the cyclohexyl or phenyl ring structure of Formulae I or II may be prepared by Scheme 3, below.

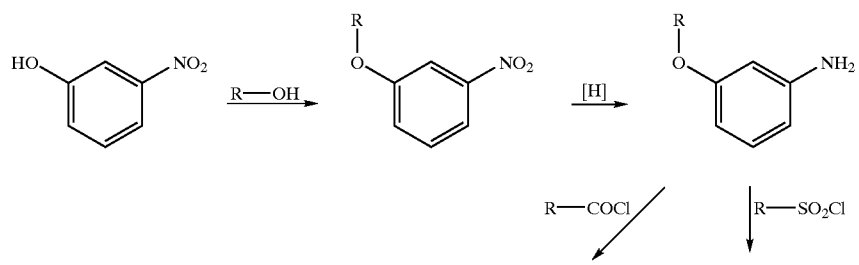

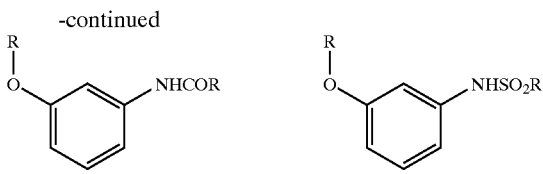

One skilled in the art is familiar with suitable reaction conditions and parameters. The synthesis of compounds 13 and 15, detailed below, illustrates.

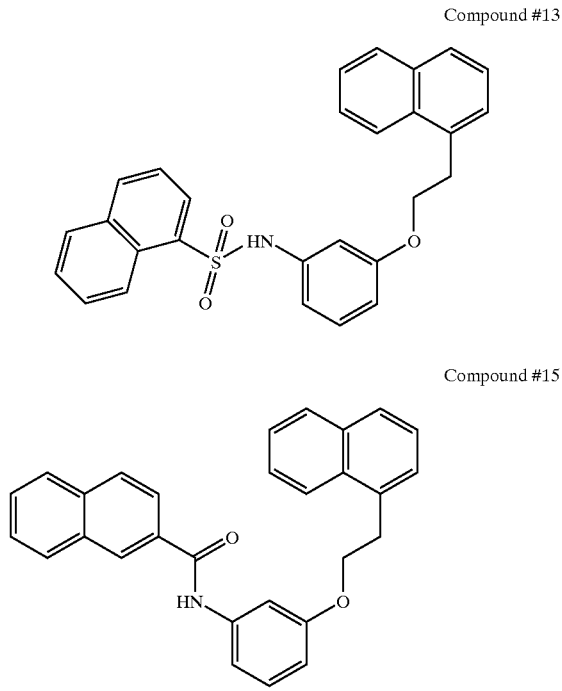

Compound #13

Compound #15

Synthesis of 1-nitro-3-(2-phenylethoxy)benzene. A stirred solution of 3-nitrophenol (1.39 g, 10 mmol), 1-naphthaleneethanol (1.89 g, 11 mmol), and triphenylphosphine (2.9 g, 11 mmol) in 100 ml of tetrahydrofuran was treated with a solution of 2.22 g (11 mmol) of diisopropylazodicarboxylate added dropwise. The resulting mixture was stirred overnight, and then concentrated and redissolved in a minimum amount of ethyl acetate. Purification on a silica gel column, eluting with 10% ethyl acetate in hexane, delivered 2.0 g of the ether.

Synthesis of 3-(2-phenylethoxy)phenylamine. To a refluxing suspension of 150 mg "wet" Raney-Nickel in 100 ml of ethanol containing 1.70 g (34 mmol) of hydrazine hydrate was added the nitro compound. After refluxing for an additional 15 minutes, the mixture was cooled and filtered through Celite to remove solids. Removal of the solvent furnished the product as an orange oil, which crystallized on standing and was used without further purification for the next step.

Synthesis of naphthyl-N-[3-(2-naphthylethoxy)phenyl] formamide, compound #15. A solution of 3-(2-phenylethoxy)phenylamine (200 mg, 0.76 mmol), 1-naphthoyl chloride (160 mg; 0.84 mmol), and triethylamine (0.2 ml, 1.43 mmol) in 50 ml of dimethylacetamide was stirred overnight. The solvent was removed and the residue dissolved in ethyl acetate and washed with water and brine. After concentration, a clear oil was obtained that crystallized on standing. This was purified on a silica gel column, eluting with methylene chloride, to obtain 200 mg of compound #15 as a white solid, Mp=191–193° C., and $^1$H NMR (DMSO, 400 MHz) peaks of: δ3.56 (t, 2H, J=6.8); 4.31 (t, 2H, J=6.9); 6.71 (dd, 1H, J=2.1, 8.1); 7.25 (t, 1H, J=8.0); 7.34 (bd, 1H, J=8.4); 7.47–8.22 (m, 15H); 10.52 (s, 1H). The theoretical atomic composition for $C_{29}H_{23}NO_2$ [C, 83.43; H, 5.55; N, 3.35] compares favorably to that found experimentally [C, 83.29; H, 5.69; N, 3.39].

Synthesis of [3-(2-naphthylethoxy)phenyl] (naphthylsulfonyl)amine, compound #13. A solution of 3-(2-phenylethoxy)phenylamine (200 mg, 0.76 mmol), 1-naphthylsulfonyl chloride (190 mg, 0.84 mmol), and triethylamine (0.2 ml, 1.43 mmol) was stirred overnight and worked up as described in the previous example. Purification of the crude product delivered 210 mg of compound 13, Mp=165–167° C., and $^1$H NMR (DMSO, 400 MHz) peaks of: δ3.42 (t, 2H, J=6.8); 4.10 (t, 2H, J=6.9); 6.48–6.60 (m, 3H); 7.01 (t, 1H, J=8.1); 7.40–8.20 (m, 13H); 8.70 (d, 1H, J=8.6); 10.68 (s, 1H). The theoretical atomic composition for $C_{28}H_{23}NSO_3$ [C, 74.15; H, 5.11; N, 3.09; S, 7.07] compares favorably with that found experimentally [C, 73.88; H, 5.05; N, 3.06; S, 7.03].

Additional examples of compounds of the invention may be prepared as depicted in Scheme 4 below.

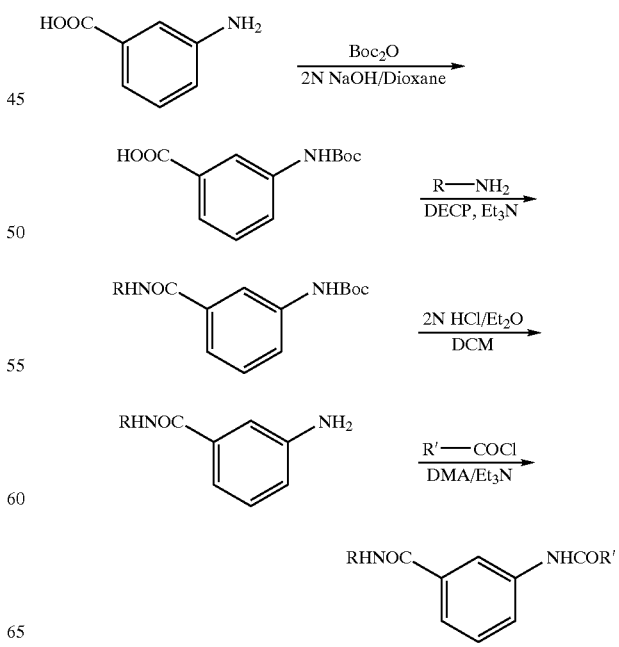

The synthesis of compound 16, detailed below, illustrates.

Compound #16

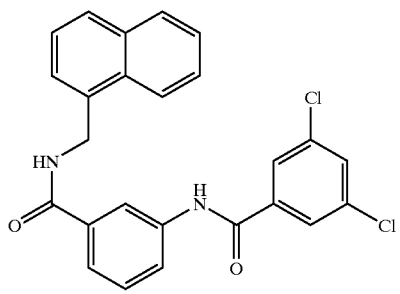

Synthesis of 3-[(tert-butoxy)carbonylamino]benzoic acid. 3-Aminobenzoic acid (5.0 g, 36.5 mmol) was dissolved in 150 ml of 2N NaOH. Dioxane (100 ml) was added, followed by 9.6 g (44 mmol) of tert-butyl dicarbonate added slowly, with stirring. After the addition was complete, the mixture was stirred overnight. It was diluted with water and washed with ether (3 portions). The aqueous phase was acidified with 20% citric acid, and the resulting purplish solid was collected by filtration and recrystallized from ethyl acetate to obtain 1.6 g of the Boc-protected amine.

Synthesis of {3-[(tert-butoxy)carbonylamino]phenyl}-N-(naphthylmethyl)formamide. A solution of 3-[(tert-butoxy)carbonylamino]benzoic acid (250 mg, 1.05 mmol), 1-naphthylmethylamine (170 mg, 1.05 mmol), diethyl cyanophosphonate (260 mg, 1.6 mmol), and triethylamine (0.22 ml, 1.6 mmol) in acetonitrile was stirred overnight. The solvent was evaporated, and the residue was partitioned between ethyl acetate and 1N HCl. The layers were separated, and the organic phase was washed twice more with 1N HCl, then 3 times each with water and brine. The solvent was removed in vacuo, and the crude product was purified on a silica gel column, eluting with 20% ethyl acetate in hexane, to deliver 270 mg of the amide.

Synthesis of {3-[(3,5-dichlorophenyl)carbonylamino]phenyl}-N-(naphthylmethyl) formamide, compound 16. {3-[(tert-Butoxy)carbonylamino]phenyl}-N-(naphthylmethyl)formamide (270 mg, 0.72 mmol) was dissolved in 25 ml of dichloromethane and treated with 7 ml of 2N HCl in ether. After stirring overnight, the precipitate was collected by filtration and dried under vacuum. The aniline (190 mg, 0.61 mmol) was dissolved in dimethylacetamide (10 ml), and 3,5-dichlorobenzoyl chloride (130 mg, 0.61 mmol) and triethylamine (0.5 mL) were added and the resulting mixture was stirred overnight. The product was worked up as described above and recrystallized from ethyl acetate to provide compound 16 as a white crystalline solid, Mp=205–208° C., and $^1$H NMR (DMSO, 400 MHz) peaks of: δ4.97 (d, 2H, J=5.76); 7.45–8.26 (m, 14H); 9.10 (t, 1H, J=5.76); 10.57 (s, 1H). The theoretical atomic composition for $C_{25}H_{18}N_2O_2Cl_2$ [C, 66.83; H, 4.04; N, 6.23; Cl; 15.78] compares favorably with that found experimentally [C, 66.73; H, 4.15; N, 6.16; Cl, 15.81].

Exemplary Ways to Detect Binding to a CyP

Measuring the Inhibition of Rotamase (prolyl peptidyl cis-trans isomerase) Activity A number of substrates for rotamase are known in the art or can be derived from those known. Typically, the substrate contacts a sample containing a protein with rotamase activity and the conversion of the substrate is detected after a period of time. The method for detecting conversion of the substrate will vary with the particular substrate chosen. One method has been termed the $K_i$ test (See Harding, et al., Nature, 341:758–760 (1989); and Holt et al., J. Am. Chem. Soc., 115:9923–9938). The cis-trans isomerization of an alanine-proline bond in a model substrate, N-succinyl-Ala-Ala-Pro-Phe-p-nitroanilide, is monitored spectrophotometrically in a chymotrypsin-coupled assay. The action of chymotrypsin releases p-nitroaniline from only the trans form of the substrate. The amount of p-nitroaniline can be monitored in a spectrophotometer, for example. Other methods of detecting the presence of p-nitroaniline can also be used. The inhibition of this reaction caused by different concentrations of inhibitor is determined and the data is analyzed as a change in first-order rate constant as a function of inhibitor concentration, which yield the $K_i$ value.

The following are added to a plastic cuvette: 950 mL of ice cold assay buffer (25 mM HEPES, pH 7.8, 100 mM NaCl), 10 μL of CyP A (2.5 μM in 10 mM Tris-Cl pH 7.5, 100 mM NaCl, 1 mM dithiothreitol), 25 μL of chymotrypsin (50 mg/ml in 1 mM HCl), and 10 μL of test compound, at various concentrations, in dimethyl sulfoxide. The reaction is initiated by the addition of 5 μL of substrate (succinyl-Ala-Phe-Pro-Phe-para-nitroanilide, 5 mg/mL in 470 mM LiCl in trifluoroethanol). The absorbance at 390 nm versus time is monitored for 90 seconds using a spectrophotometer and the rate constants are determined from the absorbance versus time data files.

Data obtained for representative compounds are presented in the following Table.

| Compd | % Inhibition at 10 μM | $IC_{50}$ (μM) |
|---|---|---|
| 1 | 100 | 6 |
| 3 | 100 | 0.6 |
| 4 | 100 | 0.80 |
| 6 | 100 | 1.02 |
| 7 | 100 | 1.9 |
| 10 | 99 | 4.5 |
| 11 | 93 | 4.0 |
| 12 | 47.7 | 9.5 |
| 13 | 100 | 0.83 |
| 14 | 100 | 0.97 |
| 15 | 100 | 0.74 |
| 16 | 100 | 1.0 |
| 17 | 99 | 0.65 |
| 18 | 100 | 0.52 |
| 19 | 98 | 2.9 |
| 20 | 100 | 4.85 |
| 21 | 100 | 1.92 |
| 22 | 100 | 8.2 |
| 23 | 100 | 4.2 |
| 24 | 100 | 5.09 |
| 25 | 100 | 3.25 |
| 26 | 100 | 5.64 |
| 27 | 100 | 8.55 |
| 28 | 100 | 2.95 |
| 29 | 89 | 6.2 |
| 30 | 88 | 3.95 |
| 31 | 100 | 3.9 |
| 32 | None detected | — |
| 33 | 2 | |

The inhibition values refer to the percent of rotamase activity that is inhibited by the compound when the compound is present at a concentration of 10 μM. The higher the percentage, the more the compound inhibits rotamase, which in turn means the more active the compound is at binding or interacting with CyP. The $IC_{50}$ values refer to the concentration that inhibits 50% of the rotamase activity in a sample. The lower the value, the more active the compound is at binding or interacting with CyP. While CyP A is used in these examples, other CyP proteins can be substituted.

Similar methods can be used with other immunophilins, such as the FKBPs, to demonstrate the presence or absence of FKBP binding activity. Preferred compounds have an $IC_{50} \leq 1$ μM for inhibition of cyclophilin rotamase activity. Epecially preferred compounds may also have an $IC_{50} \geq 10$ μM, or $\geq 50$ μM, for inhibition of FKBP rotamase activity.

Measuring the Neuroactivity of the Compounds of the Invention

As noted above, a number of methods can be used to assay for the bioactivity of the compounds of the invention. These assays can be in vivo or in vitro methods. The examples below illustrate assays for the ability of the compounds to protect neuronal cells from toxic treatments and the ability of the compounds to elicit neuronal cell growth, regeneration, or neurite extension.

Immunostaining and Neurite Outgrowth Quantitation

Spinal cord and dorsal root ganglion (DRG) cells from adult mice can be isolated by micro-dissection. The spinal cord with attached DRGs from an adult mouse (15–10 g) is removed. Spinal nerves are cut away using micro-dissection scissors and any excess material is trimmed until the DRG is free. Using sharp micro-dissecting scissors, a transverse cut is made in the peripheral nerve, leaving 1–2 mm attached, and the explant placed into Petri dish and covered with plating media. When finished collecting all DRGs, the spinal nerve is trimmed to about 1 mM in length. Then embed the explant in 30 μL of reduced growth factor Matrigel on a circular coverslip, and place in a 35 mM culture dish. Cover the sensory ganglion explant with 2 mls of media. Compounds, drugs or control solutions are added from 10× stocks, and incubated at 37° C., 5% $CO_2$, 95% humidity for 48 hrs. Wash cultures twice with PBS, and fix with 10% formalin for 30 minutes. Wash the fixed cultures twice with PBS and store refrigerated in PBS.

Place cultures in Block Buffer (5% Horse Serum, 5% Goat Serum, 1% Triton X, PBS pH=7.4) overnight, while rotating, at a temperature of 4° C. Add primary antibody (Beta tubulin, Sigma Chemical Co.) diluted in Block Buffer and incubate overnight at 4° C. Wash 5 times with PBS and apply secondary antibody (Alexa 488 Goat Anti-Mouse) diluted in block buffer. Incubate overnight at 4° C. Wash 5 times with PBS and leave overnight at 4 degrees. Coverslip the cultures and measure total neurite length from the end of the attached spinal nerve. Lengths of all neurites are quantitated and compared to those present in vehicle-treated control DRGs.

Typical results are shown in FIGS. 8–10.

Neuroprotection Assay

All cultures were derived from postnatal day 8 (P8) Sprague-Dawley rat lumbar spinal cord slices of 325 micron thickness. Each experiment consisted of two 6-well plates with 5 slices from 4 different animals per well. Media changes were performed every 3 to 4 days. Cultures were treated with THA [L(–)-threo-3-hydroxyaspartic acid; Tocris Cookson Inc., Ballwin, Mo.] at 200 μM+compound (10 μM) after one week in culture. The control was an untreated sample with 0.1% DMSO as vehicle. The THA control was a THA treated sample with 0.1% DSMO as vehicle. Two wells were used per condition. One media change with new THA and compounds was performed. The experiment was stopped 6 to 8 days following drug treatment (13–15 total days in vitro, DIV) as dictated by visual assessment of lesion, by fixation with 4% paraformaldehyde/0.1 M phosphate buffer for 30 minutes. Slices were permeabilized with 100% cold methanol for 10 minutes. Slices were transferred to staining wells. The slices were blocked with 10% HS/TBS. Primary antibody incubation was overnight at 4° C. with SMI-32 antibody 1:5000 in 2% HS/TBS. SMI-32 was specific towards unphosphorylated H neurofilament subunit. Vectastain ABC Elite Kit with rat absorbed anti-mouse secondary antibody was used with DAB to stain the slices. The slices were mounted onto a slide and a coverslip was sealed with DPX mounting solution.

Quantification of surviving neurons was performed on a Ziess Axiovert microscope. Neuronal survival was determined by observing an intact neuronal cell body with processes located ventrally of the central canal in each hemisphere. This correlated to laminae VII, VIII and IX. Each hemisphere was counted individually. The statistics were performed with StatView software on a minimum of three different experiments per condition and significance was determined as compared to THA control. The percent of protection was determined from the average number of living neurons by the following equation: (drug treatment condition–THA control)/(Untreated control–THA control).

Typical results are shown in FIGS. 1–7.

As noted above, the specific examples should not be interpreted as a limitation to the scope of the invention. Instead, they are merely exemplary embodiments one skilled in the art would understand from the entire disclosure of this invention.

REFERENCES CITED

Each of the references cited below or in the text above can be relied on to make and use any aspect of this invention. While particular uses and references are discussed above, this should not be taken as a limitation on the use of any particular reference. All the references are specifically included into this text by reference, in their entirety.

Holt et al., *Bioorg. Med. Chem. Letters,* 4: 315–320 (1994);
Steiner et al., *PNAS* 94:2019–2024 (1997);
Hamilton and Steiner, *J. of Med. Chem.* 41: 5119–5143 (1998);
Gold, *Mol. Neurobiol.* 15: 285–306 (1997);
Hamilton, et al., *Bioorgan. Med.Chem.Lett.* 7:1785–1790 (1997);
McMahon, et al., *Curr. Opin. Neurobiol.* 5:616–624 (1995);
Gash, et al., *Nature* 380:252–255 (1996);
Gerlach, et al., *Eur. J. Pharmacol.-Mol. Pharmacol.* 208:273–286 (1991);
Apfel, et al., *Brain Res.* 634:7–12 (1994);
Wang, et al., *J. Pharmacol. Exp. Therap.* 282:1084–1093 (1997);
Gold, et al., *Exp. Neurol.* 147:269–278 (1997);
Hoffer et al., *J. Neural Transm. [Suppl.]* 49:1–10 (1997);
Lyons, et al., *PNAS* 91:3191–3195 (1994);
Fischer, et al., *Biomed. Biochem. Acta* 43:1101–1112 (1984);
Kofron, et al., *Biochem.* 30:6127–6134 (1991);
Kofron et al., *J. Am. Che. Soc.* 114:2670–2675 (1992);
Harrison et al., *Biochem.* 29:3813–3816 (1990);
Lang et al., *Nature* 329:268–270 (1987);
Mucke et al., *Biochem.* 31:7848–7854 (1992);
Schonbrunner et al., *J. Biol. Chem.*266:3630–3635 (1991);
Hsu et al., *J. Am. Chem. Soc.* 112:6745–6747 (1990);
Justice et al., *Biochem. Biophys. Res. Commun.* 171:445–450 (1990);
Fingl et al., in *The Pharmacological Basis of Therapeutics,* Ch. 1, (1975);
*Remington's Pharmaceutical Sciences,* Mack Publishing Co., Easton, Pa., 18$^{th}$ edition (1990);
Maurer, et al. *Am. J. Pathol.* 150(4):1433–41 (1997);
Ausubel, et al., eds., *Current Protocols in Molecular Biology,* John Wiley & Sons, N.Y., (and supplements through June 1999);

Coligan, et al., eds., *Current Protocols in Immunology*, John Wiley and Sons, N.Y., (and supplements through June 1999); and Enna et al., eds., *Current Protocols in Pharmacology*, John Wiley & Sons, N.Y., (and supplements through June 1999).

We claim:

1. A complex comprising a compound of Formula II and a cyclophilin, wherein Formula II is

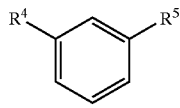

where $R^4$ and $R^5$ may independently be
—N—$SO_2$—R,
—$SO_2$—NRR,
—O—R,
—CO—N—R,
—N—CO—R,
—CO—R, wherein each of R may independently be hydrogen, Q, or C1–C6 branched or straight alkyl or alkenyl chain, which may be substituted in one or more positions by C3–C8 cycloalkyl or cycloalkenyl, hydroxyl, or carbonyl oxygen, and where in said alkyl or alkenyl chain one or more carbon atoms are either optionally substituted with Q, or optionally replaced by O, S, SO, $SO_2$, N, or NH;

where Q, which is optionally saturated, partially saturated, or aromatic, is a mono-, bi-, or tricyclic, carbo- or heterocyclic ring, wherein each ring may be optionally substituted in one to five positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

2. The complex of claim 1 wherein each R of $R^4$ and $R^5$ in said compound of Formula II may independently be hydrogen, Q, or C1–C6 branched or straight chain alkyl or alkenyl, which may be substituted in one or more positions by C3–C8 cycloalkyl or cycloalkenyl, hydroxyl, carbonyl oxygen, or Q;

where Q, which is optionally aromatic, is a mono-, bi-, or tricyclic, carbo- or heterocyclic ring, wherein each ring may be optionally substituted in one to three positions with halo, hydroxyl, nitro, trifluoromethyl, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

3. The complex of claim 1, wherein the cyclophilin is a human cyclophilin.

4. The complex of claim 2, wherein the cyclophilin is a human cyclophilin.

5. A method of using a compound to bind a cyclophilin-type immunophilin protein, comprising contacting the compound with a cyclophilin, wherein the compound has the following formula:

Formula II

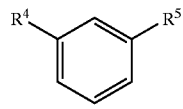

where $R^4$ and $R^5$ may independently be
—N—$SO_2$—R,
—$SO_2$—NRR,
—O—R,
—CO—N—R,
—N—CO—R,
—CO—R, wherein each R may independently be hydrogen, Q, or a C1–C6 branched or straight alkyl or alkenyl chain, which may be substituted in one or more positions by C3–C8 cycloalkyl or cycloalkenyl, hydroxyl, or carbonyl oxygen, and where in said alkyl or alkenyl chain one or more carbon atoms are either optionally substituted with Q, or optionally replaced by O, S, SO, $SO_2$, N, or NH;

where Q, which is optionally saturated, partially saturated, or aromatic, is a mono-, bi-, or tricyclic, carbo- or heterocyclic ring, wherein each ring may be optionally substituted in one to five positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

6. The method of claim 5, wherein the compound inhibits cyclophilin rotamase activity with an $IC_{50}$ of 1 μM or less.

7. The method of claim 5, wherein each R of $R^4$ and $R^5$ in said compound of Formula II may independently be hydrogen, Q, or C1–C6 branched or straight chain alkyl or alkenyl, which may be substituted in one or more positions by C3–C8 cycloalkyl or cycloalkenyl, hydroxyl, carbonyl oxygen, or Q;

where Q, which is optionally aromatic, is a mono-, bi-, or tricyclic, carbo- or heterocyclic ring, wherein each ring may be optionally substituted in one to three positions with halo, hydroxyl, nitro, trifluoromethyl, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

8. The method of claim 7, wherein the compound inhibits cyclophilin rotamase activity with an $IC_{50}$ of 1 μM or less.

9. The method of claim 5, wherein the compound inhibits FKBP rotamase activity with an $IC_{50}$ of 10 μM or more.

10. The method of claim 7, wherein the compound inhibits FKBP rotamase activity with an $IC_{50}$ of 10 μM or more.

11. The method of claim 5, wherein contacting the compound with a cyclophilin occurs in vivo.

12. The method of claim 7, wherein contacting the compound with a cyclophilin occurs in vivo.

13. The method of claim 5, wherein contacting the compound with a cyclophilin occurs within a cell.

14. The method of claim 7, wherein contacting the compound with a cyclophilin occurs within a cell.

15. The method of claim 5, wherein the cyclophilin is a human cyclophilin.

16. The method of claim 7, wherein the cyclophilin is a human cyclophilin.

17. The method of claim 5, wherein contacting the compound with a cyclophilin occurs after administering the compound to an animal.

18. The method of claim 7, wherein contacting the compound with a cyclophilin occurs after administering the compound to an animal.

19. The method of claim 17, wherein the animal is human.

20. The method of claim 18, wherein the animal is human.

21. The method of claim 19, wherein the human is diagnosed with, is predisposed to, or is suspected of having a neurodegenerative condition, a neuropathic condition, or a peripheral neuropathy.

22. The method of claim 20, wherein the human is diagnosed with, is predisposed to, or is suspected of having a neurodegenerative condition, a neuropathic condition, or a peripheral neuropathy.

23. The method of claim 19, wherein the human has Parkinson's disease, Alzheimer's disease, ALS, memory loss, hair loss, hearing loss, vision loss, stroke, peripheral neuropathy, diabetic neuropathy, mitochondrial disorder, viral infection, traumatic brain injury, or a spinal cord injury.

24. The method of claim 20, wherein the human has Parkinson's disease, Alzheimer's disease, ALS, memory loss, hair loss, hearing loss, vision loss, stroke, peripheral neuropathy, diabetic neuropathy, mitochondrial disorder, viral infection, traumatic brain injury, or a spinal cord injury.

25. A method of using a compound of Formula II to treat or prevent a neurological disorder in an animal, comprising administering a pharmaceutically effective amount of the compound to the animal, wherein Formula II is

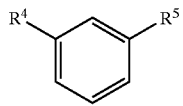

where $R^4$ and $R^5$ may independently be
—N—SO$_2$—R,
—SO$_2$—NRR,
—O—R,
—CO—N—R,
—N—CO—R,
—CO—R,
wherein each of R may independently be
hydrogen, Q, or C1–C6 branched or straight alkyl or alkenyl chain, which may be substituted in one or more positions by C3–C8 cycloalkyl or cycloalkenyl, hydroxyl, or carbonyl oxygen, and where in said alkyl or alkenyl chain one or more carbon atoms are either optionally substituted with Q, or optionally replaced by O, S, SO, SO$_2$, N, or NH;
where Q, which is optionally saturated, partially saturated, or aromatic, is a mono-, bi-, or tricyclic, carbo- or heterocyclic ring, wherein each ring may be optionally substituted in one to five positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

26. The method of claim 25, wherein each R of $R^4$ and $R^5$ in said compound of Formula II may independently be
hydrogen, Q, or C1–C6 branched or straight chain alkyl or alkenyl, which may be substituted in one or more positions by C3–C8 cycloalkyl or cycloalkenyl, hydroxyl, carbonyl oxygen, or Q;
where Q, which is optionally aromatic, is a mono-, bi-, or tricyclic, carbo- or heterocyclic ring, wherein each ring may be optionally substituted in one to three positions with halo, hydroxyl, nitro, trifluoromethyl, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

27. The method of claim 25, wherein the animal is human.

28. The method of claim 26, wherein the animal is human.

29. The method of claim 27, wherein the human is diagnosed with, is predisposed to, or is suspected of having a neurodegenerative condition, a neuropathic condition, or a peripheral neuropathy.

30. The method of claim 28, wherein the human is diagnosed with, is predisposed to, or is suspected of having a neurodegenerative condition, a neuropathic condition, or a peripheral neuropathy.

31. The method of claim 27, wherein the human has Parkinson's disease, Alzheimer's disease, ALS, memory loss, hair loss, hearing loss, vision loss, stroke, peripheral neuropathy, diabetic neuropathy, mitochondrial disorder, viral infection, traumatic brain injury, or a spinal cord injury.

32. The method of claim 28, wherein the human has Parkinson's disease, Alzheimer's disease, ALS, memory loss, hair loss, hearing loss, vision loss, stroke, peripheral neuropathy, diabetic neuropathy, mitochondrial disorder, viral infection, traumatic brain injury, or a spinal cord injury.

33. A method of preventing a neurodegenerative condition comprising administering to an animal an effective amount of a composition comprising a compound of Formula II and a pharmaceutically acceptable carrier, diluent, or excipient, wherein Formula II is

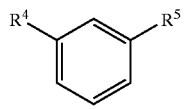

where $R^4$ and $R^5$ may independently be
—N—SO$_2$—R,
—SO$_2$—NRR,
—O—R,
—CO—N—R,
—N—CO—R,
—CO—R,
wherein each of R may independently be hydrogen, Q, or C1–C6 branched or straight alkyl or alkenyl chain, which may be substituted in one or more positions by C3–C8 cycloalkyl or cycloalkenyl, hydroxyl, or carbonyl oxygen, and where in said alkyl or alkenyl chain one or more carbon atoms are either optionally substituted with Q, or optionally replaced by O, S, SO, SO$_2$, N, or NH;

where Q, which is optionally saturated, partially saturated, or aromatic, is a mono-, bi-, or tricyclic, carbo- or heterocyclic ring, wherein each ring may be optionally substituted in one to five positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

34. A method of preventing a neurodegenerative condition comprising administering to an animal an effective amount of a composition comprising a compound of Formula II and a pharmaceutically acceptable carrier, diluent, or excipient, wherein Formula II is

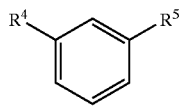

where R$^4$ and R$^5$ may independently be
—N—SO$_2$—R,
—SO$_2$—NRR,
—O—R,
—CO—N—R,
—N—CO—R,
—CO—R, wherein each of R may independently be
hydrogen, Q, or C1–C6 branched or straight chain alkyl or alkenyl, which may be substituted in one or more positions by C3–C8 cycloalkyl or cycloalkenyl, hydroxyl, carbonyl oxygen, or Q;
where Q, which is optionally aromatic, is a mono-, bi-, or tricyclic, carbo- or heterocyclic ring, wherein each ring may be optionally substituted in one to three positions with halo, hydroxyl, nitro, trifluoromethyl, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

35. A method of protecting nerves from damage comprising administering to an animal an effective amount of a composition comprising a compound of Formula II and a pharmaceutically acceptable carrier, diluent, or excipient, wherein Formula II is

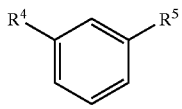

where R$^4$ and R$^5$ may independently be
—N—SO$_2$—R,
—SO$_2$—NRR,
—O—R,
—CO—N—R,
—N—CO—R,
—CO—R,
wherein each of R may independently be
hydrogen, Q, or C1–C6 branched or straight alkyl or alkenyl chain, which may be substituted in one or more positions by C3–C8 cycloalkyl or cycloalkenyl, hydroxyl, or carbonyl oxygen, and where in said alkyl or alkenyl chain one or more carbon atoms are either optionally substituted with Q, or optionally replaced by O, S, SO, SO$_2$, N, or NH;
where Q, which is optionally saturated, partially saturated, or aromatic, is a mono-, bi-, or tricyclic, carbo- or heterocyclic ring, wherein each ring may be optionally substituted in one to five positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

36. A method of protecting nerves from damage comprising administering to an animal an effective amount of a composition comprising a compound of Formula II and a pharmaceutically acceptable carrier, diluent, or excipient, wherein Formula II is

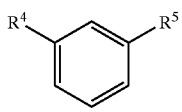

where R$^4$ and R$^5$ may independently be
—N—SO$_2$—R,
—SO$_2$—NRR,
—O—R,
—CO—N—R,
—N—CO—R,
—CO—R,
wherein each of R may independently be
hydrogen, Q, or C1–C6 branched or straight chain alkyl or alkenyl, which may be substituted in one or more positions by C3–C8 cycloalkyl or cycloalkenyl, hydroxyl, carbonyl oxygen, or Q;
where Q, which is optionally aromatic, is a mono-, bi-, or tricyclic, carbo- or heterocyclic ring, wherein each ring may be optionally substituted in one to three positions with halo, hydroxyl, nitro, trifluoromethyl, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

37. A method of stimulating the growth of or regenerating damaged nerves comprising administering to an animal an effective amount of a composition comprising a compound of Formula II and a pharmaceutically acceptable carrier, diluent, or excipient, wherein Formula II is

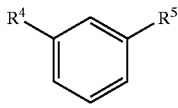

where $R^4$ and $R^5$ may independently be
—N—SO$_2$—R,
—SO$_2$—NRR,
—O—R,
—CO—N—R,
—N—CO—R,
—CO—R,
wherein each of R may independently be
hydrogen, Q, or C1–C6 branched or straight alkyl or alkenyl chain, which may be substituted in one or more positions by C3–C8 cycloalkyl or cycloalkenyl, hydroxyl, or carbonyl oxygen, and where in said alkyl or alkenyl chain one or more carbon atoms are either optionally substituted with Q, or optionally replaced by O, S, SO, SO$_2$, N, or NH;
where Q, which is optionally saturated, partially saturated, or aromatic, is a mono-, bi-, or tricyclic, carbo- or heterocyclic ring, wherein each ring may be optionally substituted in one to five positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

38. A method of stimulating the growth of or regenerating damaged nerves comprising administering to an animal an effective amount of a composition comprising a compound of Formula II and a pharmaceutically acceptable carrier, diluent, or excipient, wherein Formula II is

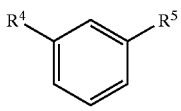

where $R^4$ and $R^5$ may independently be
—N—SO$_2$—R,
—SO$_2$—NRR,
—O—R,
—CO—N—R,
—N—CO—R,
—CO—R,
wherein each of R may independently be
hydrogen, Q, or C1–C6 branched or straight chain alkyl or alkenyl, which may be substituted in one or more positions by C3–C8 cycloalkyl or cycloalkenyl, hydroxyl, carbonyl oxygen, or Q;
where Q, which is optionally aromatic, is a mono-, bi-, or tricyclic, carbo- or heterocyclic ring, wherein each ring may be optionally substituted in one to three positions with halo, hydroxyl, nitro, trifluoromethyl, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

\* \* \* \* \*